United States Patent
Oyola et al.

(10) Patent No.: US 9,901,410 B2
(45) Date of Patent: Feb. 27, 2018

(54) SURGICAL POSITIONING AND SUPPORT SYSTEM

(75) Inventors: Arnold Oyola, Northborough, MA (US); Joseph Stand, Holden, MA (US); Kevin Gilmartin, Boston, MA (US); Ian Darisse, Newport, MA (US); Robert Didomenico, Norfolk, MA (US); J. Christopher Flaherty, Topsfield, MA (US)

(73) Assignee: Medrobotics Corporation, Raynham, MA (US)

( * ) Notice: Subject to any disclaimer, the term of this patent is extended or adjusted under 35 U.S.C. 154(b) by 98 days.

(21) Appl. No.: 13/812,324

(22) PCT Filed: Jul. 21, 2011

(86) PCT No.: PCT/US2011/044811
§ 371 (c)(1),
(2), (4) Date: Sep. 17, 2013

(87) PCT Pub. No.: WO2012/015659
PCT Pub. Date: Feb. 2, 2012

(65) Prior Publication Data
US 2014/0012287 A1     Jan. 9, 2014

Related U.S. Application Data

(60) Provisional application No. 61/368,257, filed on Jul. 28, 2010.

(51) Int. Cl.
*A61B 34/30* (2016.01)
*A61B 1/008* (2006.01)
(Continued)

(52) U.S. Cl.
CPC .............. *A61B 34/30* (2016.02); *A61B 34/76* (2016.02); *A61B 90/50* (2016.02); *A61B 1/0055* (2013.01);
(Continued)

(58) Field of Classification Search
CPC ................ A61B 19/2203; A61B 17/24; A61B 2017/3445; A61B 2017/00314;
(Continued)

(56) References Cited

U.S. PATENT DOCUMENTS 3,060,972 A   10/1962   Sheldon
3,557,780 A    1/1971   Sato
(Continued)

FOREIGN PATENT DOCUMENTS

EP      653922      11/2005
EP     1015068       9/2011
(Continued)

OTHER PUBLICATIONS

International Search Report dated Apr. 6, 2012, issued in corresponding International Application No. PCT/US2011/044811.
(Continued)

*Primary Examiner* — Christopher L Templeton
*Assistant Examiner* — George J Ulsh
(74) *Attorney, Agent, or Firm* — Onello & Mello, LLP.

(57) ABSTRACT

A system for performing a medical procedure is provided comprising at least one tool and a tool support for supporting a distal portion of the tool. An operator manipulates a human interface device and produces control signals sent to a controller. The controller manipulates the tool support based on the received control signals.

19 Claims, 15 Drawing Sheets

(51) Int. Cl.
*A61B 90/50* (2016.01)
*A61B 1/005* (2006.01)
*A61B 17/24* (2006.01)
*A61B 17/00* (2006.01)
*A61B 17/34* (2006.01)
*A61B 34/00* (2016.01)
*A61B 90/00* (2016.01)
*A61B 90/30* (2016.01)

(52) U.S. Cl.
CPC ..... *A61B 17/24* (2013.01); *A61B 2017/00314* (2013.01); *A61B 2017/3445* (2013.01); *A61B 2017/3447* (2013.01); *A61B 2034/302* (2016.02); *A61B 2034/715* (2016.02); *A61B 2034/742* (2016.02); *A61B 2090/309* (2016.02); *A61B 2090/3614* (2016.02); *A61B 2090/508* (2016.02)

(58) Field of Classification Search
CPC .... A61B 2019/2246; A61B 2019/2215; A61B 1/0055; A61B 1/008; A61B 1/0057; A61M 2025/0161; A61M 25/0133; A61M 25/0147
USPC ....................................................... 606/130
See application file for complete search history.

(56) References Cited

U.S. PATENT DOCUMENTS

| | | |
|---|---|---|
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,643,653 A | 2/1972 | Takahashi et al. |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hill |
| 4,479,914 A | 10/1984 | Baumrucker |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A | 4/1987 | Iwashita |
| 4,661,032 A | 4/1987 | Arai |
| 4,666,366 A | 5/1987 | Davis |
| 4,700,693 A | 10/1987 | Lia et al. |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,180,276 A | 1/1993 | Hendrickson |
| 5,193,963 A | 3/1993 | McAffee et al. |
| 5,195,968 A | 3/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,386,741 A | 2/1995 | Rennex |
| 5,448,989 A | 9/1995 | Heckele |
| 5,524,180 A | 6/1996 | Wang et al. |
| 5,759,151 A | 6/1998 | Sturges |
| 6,080,181 A | 6/2000 | Jensen et al. |
| 6,120,433 A | 9/2000 | Mizuno et al. |
| 6,132,368 A | 10/2000 | Cooper |
| 6,223,100 B1 | 4/2001 | Green |
| 6,234,958 B1 | 5/2001 | Snoke et al. |
| 6,270,453 B1 * | 8/2001 | Sakai .................. A61B 1/0055 600/141 |
| 6,346,072 B1 | 2/2002 | Cooper |
| 6,440,061 B1 | 8/2002 | Wenner et al. |
| 6,450,948 B1 | 9/2002 | Matsuura et al. |
| 6,743,239 B1 | 6/2004 | Kuehn et al. |
| 6,837,846 B2 | 1/2005 | Jaffe et al. |
| 6,837,847 B2 | 1/2005 | Ewers et al. |
| 6,916,306 B1 | 7/2005 | Jenkins et al. |
| 7,182,764 B2 | 2/2007 | Jenkins et al. |
| 7,217,246 B1 | 5/2007 | Stone |
| 7,575,548 B2 * | 8/2009 | Takemoto .......... A61B 1/00087 600/104 |
| 7,789,875 B2 | 9/2010 | Brock et al. |
| 7,850,642 B2 | 12/2010 | Moll et al. |
| 7,854,109 B2 | 12/2010 | Zubiate et al. |
| 7,854,738 B2 | 12/2010 | Lee et al. |
| 7,867,241 B2 | 1/2011 | Brock et al. |

(56) References Cited

U.S. PATENT DOCUMENTS

| | | | |
|---|---|---|---|
| 7,918,845 B2 | 4/2011 | Saadat et al. | |
| 7,946,546 B2 | 5/2011 | Zubiate et al. | |
| 8,075,476 B2 | 12/2011 | Vargas | |
| 8,100,031 B2 | 1/2012 | Zubiate et al. | |
| 8,192,422 B2 | 6/2012 | Zubiate et al. | |
| 8,459,138 B2 | 6/2013 | Zubiate et al. | |
| 9,011,318 B2 | 4/2015 | Choset et al. | |
| 9,591,964 B2 | 3/2017 | Choset et al. | |
| 2001/0013764 A1 | 8/2001 | Blumenkranz et al. | |
| 2002/0133174 A1 | 9/2002 | Charles et al. | |
| 2002/0161281 A1 | 10/2002 | Jaffe et al. | |
| 2003/0135203 A1 | 7/2003 | Wang et al. | |
| 2004/0138525 A1 | 7/2004 | Saadat et al. | |
| 2004/0138529 A1 | 7/2004 | Wiltshire et al. | |
| 2004/0193146 A1 | 9/2004 | Lee et al. | |
| 2005/0033287 A1 | 2/2005 | Sra | |
| 2005/0065397 A1 | 3/2005 | Saadat et al. | |
| 2005/0090811 A1 | 4/2005 | Doyle et al. | |
| 2005/0113640 A1 | 5/2005 | Saadat et al. | |
| 2005/0215992 A1 | 9/2005 | Jenkins et al. | |
| 2005/0216033 A1 | 9/2005 | Lee et al. | |
| 2005/0228224 A1* | 10/2005 | Okada | A61B 1/00071 600/104 |
| 2006/0052664 A1 | 3/2006 | Julian et al. | |
| 2006/0258906 A1 | 11/2006 | Binmoeller | |
| 2007/0299387 A1 | 12/2007 | Williams et al. | |
| 2008/0027279 A1 | 1/2008 | Abou El Kheir | |
| 2008/0119868 A1 | 5/2008 | Sharp et al. | |
| 2008/0163603 A1 | 7/2008 | Zubiate et al. | |
| 2008/0188869 A1 | 8/2008 | Weitzner et al. | |
| 2008/0245173 A1 | 10/2008 | Schwerin et al. | |
| 2009/0030428 A1 | 1/2009 | Omori et al. | |
| 2009/0171151 A1 | 7/2009 | Choset et al. | |
| 2009/0287043 A1 | 11/2009 | Naito et al. | |
| 2010/0063354 A1 | 3/2010 | Hashimoto et al. | |
| 2010/0160735 A1 | 6/2010 | Bakos | |
| 2010/0160736 A1 | 6/2010 | Padget et al. | |
| 2010/0204713 A1 | 8/2010 | Ruiz Morales | |
| 2010/0224022 A1 | 9/2010 | Choi et al. | |
| 2010/0280325 A1 | 11/2010 | Ibrahim et al. | |
| 2011/0028790 A1 | 2/2011 | Farr et al. | |
| 2011/0056320 A1 | 3/2011 | Zubiate et al. | |
| 2011/0152613 A1 | 6/2011 | Zubiate et al. | |
| 2011/0184241 A1 | 7/2011 | Zubiate et al. | |
| 2011/0213384 A1 | 9/2011 | Jeong | |
| 2011/0313243 A1 | 12/2011 | Zubiate et al. | |
| 2012/0209073 A1 | 8/2012 | McWeeney et al. | |
| 2013/0150673 A1 | 6/2013 | Kakehashi | |
| 2014/0088356 A1 | 3/2014 | Matsuo et al. | |
| 2015/0164491 A1 | 6/2015 | Choset et al. | |
| 2016/0174816 A1 | 6/2016 | Choset et al. | |
| 2017/0156569 A1 | 6/2017 | Choset et al. | |

FOREIGN PATENT DOCUMENTS

| | | |
|---|---|---|
| JP | H08117238 | 5/1996 |
| JP | 2000037390 | 2/2000 |
| JP | 2004181031 | 7/2004 |
| JP | 2006087687 | 4/2006 |
| JP | 2008504072 | 2/2008 |
| JP | 2008540041 | 11/2008 |
| WO | 2006124880 | 11/2006 |
| WO | 2006083306 | 4/2008 |
| WO | 2009149421 | 12/2009 |
| WO | 201050771 | 5/2010 |

OTHER PUBLICATIONS

PCT ISRWO dated May 19, 2014, issued in International application No. PCT/US2014/010808.

Expo-70 Robot—Vadim Matskevich's students, http://cyberneticzoo.com/wp-content/uploads/2010/03/Expo-70-MK-1969-02-p31-3.pdf, 1969.

Conductor Robot, http://cyberneticzoo.com/wp-content/uploads/2010/03/Ticket-robot-russian-1973.pdf, 1973.

Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.

Lee E. Weiss, Arthur C. Sanderson, Charles P. Neuman, "Dynamic Sensor Based Control of Robots with Visual Feedback", IEEE Journal of Robotics and Automation, 1987, p. 404-417.

Jean-Jacques E. Slotine, Weiping Li, "Composite adaptive control of robot manipulators", Automatica; Nonlinear Systems Laboratory, Massachusetts Institute of Technology, Cambridge, MA 02139, U.S.A., 1989, p. 509-519.

Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.

Xu Hongbin, "Stability and performance robustness analysis of hybrid control for robot manipulators", Journal of UEST of China, vol. 22 No. 5, Oct. 1993, p. 501-505.

Francois Chaumette, Patrick Rives, Bernard Espiau, "Positioning of A Robot With Respect to An Object, Tracking It and Estimating Its Velocity by Visual Servoing", IEEE International Conf. on Robotics and Automation, 1991, p. 2248-2253.

A.V. Timofejev, N.V. Ivanova, "Expert System of the Control Programs Designing of Adaptive Robots", The Lenigrand Institute of Aircraft Instrumentation, 1991, p. 912-915.

W Szczepiński, "Theory of polyhedrons of positioning accuracy of manipulators", Mechanism and Machine Theory; Institute of Fundamental Technological Research, Polish Academy of Sciences, 00-049 Warsaw, Swietokrzyska 21, Poland, 1991, p. 697-709.

Junji Furusho, Hiroshi Nagao, Naruse Makoto, "Multivariable Root Loci of Control Systems of Robot Manipulators with Flexible Driving Systems* : Distortion Feedback", JSME International Journal, 1992, p. 65-73.

Potemkin, E., Astafurov, P., Osipov, A., Malenkov, M., Mishkinyuk, V., Sologub, P., "Remote-controlled robots for repair and recovery in the zones of high radiation levels", Robotics and Automation, IEEE, 1992, p. 80-82.

S. L. Shishkin, "Adaptive control of a biped robot walking across a horizontal plane", International Journal of Adaptive Control and Signal Processing, 1992, p. 259-264.

Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.

Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.

J.D. Moon, D.W. Cho, "A component mode synthesis applied to mechanisms for an investigation of vibration", Journal of Sound and Vibration; Department of Mechanical Engineering, Pohang Institute of Science and Technology, Pohang, Korea, 1992, p. 67-79.

Timopheev, A.V., Prokhorov, D.V., "Neural networks processing systems in recognition and control problems ", Neuroinformatics and Neurocomputers; IEEE, 1992, p. 820-828.

Jianguo Fu, Naresh K. Sinha, "An iterative learning scheme for motion control of robots using neural networks: A case study", Journal of Intelligent & Robotic Systems, 1993, p. 375-398.

Troccaz, J. Lavallee, S. Hellion, E., "A passive arm with dynamic constraints: a solution to safety problems in medical robotics", Systems Engineering in the Service of Humans', Conference Proceedings, 1993, p. 166-171.

Swarup, M. Gopal, "Comparative study on linearized robot models", Journal of Intelligent & Robotic Systems, 1993, p. 287-300.

H. Azaria, A. Dvir, "Algorithm optimization using a rule-based system. A case study: The Direct Kinematic Solution in robotics", Journal of Intelligent & Robotic Systems, 1993, p. 309-324.

Erick Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.

(56) References Cited

OTHER PUBLICATIONS

K. Periyasamy, V. S. Alagar, T. D. Bui, "A formal framework for design and verification of robotic agents", Journal of Intelligent & Robotic Systems, 1993, p. 173-200.

S. Nicosia, A. Tornambé, P. Valigi, "State estimation in robotic manipulators: Some experimental results", Journal of Intelligent & Robotic Systems,, 1993, p. 321-351.

Dimitrios M. Emiris, Vassilios D. Tourassis, "Singularity-robust decoupled control of dual-elbow manipulators", Journal of Intelligent & Robotic Systems, 1993, p. 225-243.

M.M. Bayoumi, "Adaptive Control of Robots with Rigid Links: A Status Report", Department of Electrical Engineering, Queen's University, Ontario, Canada (IEEE), 1993, p. 232-236.

Y. Edan, B. A. Engel, G. E. Miles, "Intelligent control system simulation of an agricultural robot", Journal of Intelligent & Robotic Systems, 1993, p. 267-284.

Chun-Yi Su, "Adaptive sliding mode control of nonlinear robotic systems with time-varying parameters", Systems and Control Letters; Department of Mechanical Engineering, University of Victoria, Victoria, B.C. Canada V8W 3P6, 1993, p. 35-41.

Yalou Huang; Guizhang Lu, "Force Analysis and Hybrid Control Scheme for Multiple Robot Manipulators", Artificial Intelligence and Robotics Research Laboratories; Dept of Computer and System Sciences; Nankai University, China (Proceedings of the 1993 IEEE/RSJ International Conference on Intelligent Robots and Systems in Japan), 1993, p. 1530-1534.

C.M. Lim; T. Hiyama, "Experimental implementation of a fuzzy logic control scheme for a servomotor", Mechatronics; Department of Electronic Engineering, Ngee Ann Polytechnic, Singapore 2159 Singapore.

E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6 2AY, U.K., 1993, p. 329-342.

A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.

L. Behera, M. Gopal, Santanu Chaudhury, "Trajectory tracking of robot manipulator using Gaussian networks", Dept. of Electrical Engineering, Indian Institute of Technology, Delhi, Hauz Khas, New Delhi 110 016, India, 1993.

E. V. Panteley, A. A. Stotsky, "Adaptive trajectory/force control scheme for constrained robot manipulators", International Journal of Adaptive Control and Signal Processing, 1993, p. 489-496.

Filaretov, V.F., "A Synthesis of Adaptive Control Systems for Industrial Robots ", Electronic Mfg Technology Symposium, 1993, p. 168-171.

S. Zenkevich, A. Maximov, A. Nazarova, A. Korshunov, "Control of robot-based assembly cell ", Lecture Notes in Control and Information Sciences , 1993, p. 418-427.

D.E. Whitney, "The Mathematics of Coordinated Control of Prosthetic Arms and Manipulators", Asme Publication, 1972.

Shapiro, "Digital Technology Enables Robots to See", Computer Design, 1978.

Bejczy, A. K., Salisbury, Jr., J. K., "Kinesthetic Coupling Between Operator and Remote Manipulator", Advances in Computer Technology, 1980.

"An Improved CT-Aided Stereotactic Neurosurgery Technique", Fifth Annual Symposium on Computer Applications in Medical Care, 1981, p. 591-595.

Michael L. Thodes, Ph.D, "Stereotactic Neurosurgery Using 3D Image Data From Computed Tomography", Journal of Medical Systems, 1982, p. 106-118.

Salisburg, Jr., J. Kenneth, "Kinematic and Force Analysis of Articulated Hands", 1982.

"Minicomputer Control Robot's Six Electrohydraulic Servoactuators", Hydraulics & Pneumatics, 1982, p. 53-58.

F.M. Kulakov, "Modeling Robot Control in Assembly Operations", Modern Robot Engineering, Moscow, MIR Publishers, 1982, p. 100-116.

Bejczy et al., "Controlling Remote Manipulators Through Kinesthetic Coupling", Computers in Mechanical Engineering, 1983, p. 48-60.

L.E. Weiss, "Dynamic Visual Servo Control of Robots: an adaptive image-based approach, Technical Report", Carnegie Mellon, 1984.

Dennis E. Bullard, "CT-Guided Stereotactic Biopsies Using a Modified Grame and Gildenberg Techniques", Journal of Neurology, Neurosurgery and Psychiatry, 1984, p. 590-595.

M. Caporali et al., "Design and Construction of a Five Fingered Robotic Hand", Robotics Age, 1984, p. 14-20.

Salisbury, Jr., J. K., "Design and Control of an Articulated Hand", International Symposium on Dessign and Synthesis, 1984.

L. Dade Lunsford, M.D., "Stereotactic Exploration of the Brain in the Era of Computed Tomography", Surg. Neurol, 1984, p. 222-230.

Jacobsen, S.C., Iversen, E.K., Knutti, D. F., Johnson, R.T., Biggers, K. B., "Design of the Utah/MIT Dexterous Hand", Conf. on Robotics and Automation, 1986.

S. Hayati, M. Mirmirani, "Improving the Absolute positioning Accuracy of Robot Manipulators", Journal of Robotic Systems, 1986, p. 397-413.

Vertut, J., Coiffet, P., "Teleoperations and Robotics Evolution and Development", Robot Technology, 1986, p. 191-194.

L.E. Weiss; A.C. Sanderson, "Dynamic Sensor-based Control of Robots with Visual Feedback", IEEE Journal of Robotics and Automation, 1987, p. 5.

Townsend, W.T., Salisbury, Jr. J. K., "The Effect of Coulomb Friction and Stiction on Force Control", Conf. on Robotics and Automation, 1987.

P. Rives, F. Chaumette, B. Espiau, "Visual Servoing Based on a Task Function Approach", International Symposium on Experimental Robotics (Canada), 1989.

B.L. Davies, R.D. Hibberd, A. Timoney, J.E.A. Wickham, "A surgeon robot for prostatectomies", Proc. of 2nd Int. Conference on Robotics in Medicine (UK), 1989.

J.T. Feddema, C.S.G. Lee, O.R. Mitchell, "Automatic selection of image features for visual servoing of a robot manipulator", Conf. IEEE Robotics and Automation (USA), 1989, p. 14-19.

J.T. Feddema, O.R. Mitchell, "Vision-Guided Servoing with Feature-Based Trajectory Generation", IEEE Transaction on Robotics and Automation, 1989.

Pierre J. de Smet, Eugene I. Rivin, Yongle Lou, D. Kegg, "Robot Performance as Influenced by Mechanical System", CIRP Annals—Manufacturing Technology, 1990, p. 383-386.

Mills, J.K., "Hybrid actuation of robotic manipulators: an integral manifold control approach", Intelligent Control, IEEE, 1990, p. 817-823.

John T. Feddema, C. S. George Lee, "Adaptive Image Feature Prediction and Control for Visual Tracking with A Hand-eye Coordinated Camera", IEEE Transactions on Systems, man, and Cybernetics, 1990, p. 1172-1183.

Rafiqul I. Noorani, "Microcomputer-based robot arm control", Mathematical and Computer Modelling, 1990, p. 450-455.

Elysseev S., Kuznetzov, N., Lukyanov A., "Control of Robot Vibrations", 1990.

C. Samson, B. Espiau, "Robot Control: The Task Function Approach", Oxford Univ., 1990.

Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.

B. Espiau, F. Chaumette, P. Rives, "A new approach to visual servoing in robotics", Research Report; IRISA/INRIA (France), 1990.

Korikov, Anatoliim, Syriamkin, Vladimiri, Titov, Vitaliis, "Correlation robot vision systems", 1990, p. 264.

Sadegh N, Hopowitz R, "Stability and robustness analysis of a class of adaptive controller for robotic manipulator", The International Journal of Robotics Research, 1990.

Rocheleau, D.N., Crane, C.D., III, "Development of a graphical interface for robotic operation in a hazardous environment", Systems, Man, and Cybernetics, 1991, p. 1077-1081.

(56) References Cited

OTHER PUBLICATIONS

J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., Kobayashi, H., "An inspection robot for feeder cables-snake like motion control", Industrial Electronics, Control, Instrumentation, and Automation, 1992, p. 849-852.
P. Kazanzides, J. Zuhars, B. Mittelsstadt, R.H. Taylor, "Force sensing and control for a surgical robot", IEEE conference on Robotics and Automation (Nice), 1992, p. 612-617.
Vsevolod I. Astafyev Farus, Yakutsk, Russia Yuri M. Gorsky, "Homeostatics", Cybernetics and applied systems, 1992, p. 7-22.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME international journal, 1992, p. 406-412.
Ph, Cinquin, et. al, IGOR: Image Guided Operating Robot. Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.
Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
Alberto Rovetta, Xia Wen, Telemanipulation Control of a Robotic Hand With Cooperating Fingers by Means of Telepresence With a Hybrid Virtual-Real Structure, RoManSy 9: Proceedings of the Ninth CISM-IFToMM Symposium on Theory and Practice of Robots and Jul. 7, 1992.
James K. Mills, Hybrid Actuator for Robot Manipulators: Design, Control and Performance, Robotics and Automation, IEEE Conference, 1993, p. 19-38.
Pietro Fanghella, Carlo Galletti, An Approach to Symbolic Kinematics of Multiloop Robot Mechanisms, RoManSy9, 1993, p. 33-40.
Yozo Fujino, Pennung Warnitchai, B.M. Pacheco, Active Stiffness Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicapped blind persons with physical guidance and activity choices", Journal of Developmental and Physical Disabilities, 1993, p. 337-348.
Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian , Generalized Dynamic Model for Multibodies Manipulator, 1993.
F.M. Kulakov, Russian Research on Robotics, Intelligent Autonomous Systems, 1995, p. 53-62.
Shevtsova N.A., Faure A., Klepatch A.A., Podladchikova L.N., Rybak I.A. , Model of Foveal Visual Preprocessor, Intelligent Robots and Computer Vision XIV: Algorithms, Techniques, Active Vision, and Materials Handling, 1995, p. 588-596.
Reynolds, O., "On Efficiency of Belts or Straps as Communicators of Work", The Engineer, 1874, p. 396.
Swift, H. W., "Power Transmission by Belts: An Investigation of Fundamentals", The Institution of Mechanical Engineers, 1928.
Smith, G. A. et al., "Surgery", 1950, p. 817-821.
"Baby Robot", http://cyberneticzoo.com/wp-content/uploads/2010/03/Ticket-robot-russian-1973.pdf, 1970.
Rajac, "Variable-Pitch Transfer Mechanism", IBM Technical Disclosure Bulletin, 1974.
ZH Luo , "Theoretical and Experimental Study on Control of Flexible Robot Arms Using Direct Strain Feedback", 1992.
Bu Yonghong, Wang Yi, "The Identification of Geometric Link Parameters of Robot Manipulators", ACTA Automatica Sinica, 1992.
Zheng Nanning Wang Long Hu chao Liu Jianqin, "Improved BP Neural Net and Its Application to Handwritten Numeral Recognition", 1992.
Stefano Chiaverini, Bruno Siciliano, Olav Egeland, Robot Control in Singular Configurations—Analysis and Experimental Results, Experimental Robotics II, 1993, p. 25-34.
Antonio Bicchi, J. Kenneth Salisbury, David L. Brock, Experimental Evaluation of Friction Characteristics With an Articulated Robotic Hand, Experimental Robotics II, 1993, p. 153-167.
Claudio Melchiorri, Gabriele Vassura, Mechanical and Control Issues for Integration of an Arm-Hand Robotic System, Experimental Robotics II, 1993, p. 136-152.
Andrew K. Rist, Ellen Y. Lin, Bartholomew O. Nnaji, Ralph Application for Surface Mount Assembly, International Journal of Flexible Manufacturing Systems, 1993, p. 27-52.
R.H. Taylor, et. al, A Model-Based Optimal Planning and Execution System With Active Sensing and Passive Manipulation for Augmentation of Human-Precision in Computer-Integrated Surgery, Lecture Notes in Control and Information Sciences; Experimental Robo.
Nobuyuki Furuya, Masatomo Matubara, An Algorithm of Motor Control by Software Servo System (2nd Report): Application to 4-AXES Scara Robot, Journal of the Japan Society of Precision Engineering , 1993, p. 423-428.
H.S. Moon, S.Y. Lee, S.J. Na, A Study on Selection of Gas Metal Arc Welding Parameters of Fillet Joints Using Neural Network, Journal of the Korean Welding Society, 1993, p. 151-160.
Byong Suk Kim, Computer—Assisted System for Accident Analysis and Mul—Function Protection in Industrial Robot, Papersearch.net (Korean Studies Information Co.), 1993, p. 61-64.
J. I. Arocena, R. W. Daniel, P. Elosegui, End Point Control of Compliant Robots, Experimental Robotics II, 1993, p. 435-449.
Ho Kyung Kim, Nonlinear Static Analysis and Determination of Initial Equilibrium States of Suspension Bridges, 1993, p. 177-186.
Gimdongha, imhyeongyo (Dong Ha Kim, Hyeon Kyo Lim) , Safe Speed Limit of Robot Arm During Teaching and Maintenance Work, 1993, p. 64-70.
Chang-Boo Kim, Seung-Hoon Lee, Inverse Dynamic Analysis of a Flexible Robot Arm With Multiple Joints by Using the Optimal Control Method, Journal of the Korean Society of Precision Engineering , 1993, p. 133-140.
Chang-Soo Han, The Optimum Design of A 6 D.O.F. Fully-Parallel Micromanipulator for Enhanced Robot Accuracy, Journal of the Korean Society of Precision Engineering , 1993, p. 42-51.
Nicholas Jackson, The Story Behind the Russian Robot Collie Patent Sketches, The Atlantic, 2011.

(56) References Cited

OTHER PUBLICATIONS

Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.
Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robot and CNC Machine System, Control R/D Team, Samsung Electronics, 1992, p. 1211-1214.
E.S. Jeon, S.H. Park, J.E. Oh, Singylarty Control of Robot Wrist Joints Using Euler Parameters, Journal of the Korean Society of Precision Engineering, 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong Kug Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using ARMA Prediction Model, 1992, p. 122-127.
Dae-Gab Gweon, Choong-Min Jung, Development of a Robot Wrist for the Assembly of Chamferless Parts, Journal of the Korean Society of Precision Engineering, 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.
Chang-Boo Kim, Seung-Hoon Lee, Formulation of the Equation of Motion for Flexible Robotics Arms by Using the Finite Element Method, Inha Univ., Daewoo Heavy Industries Ltd, 1992, p. 233-238.
Jin-Geol Kim, A Study on the Robust Digital Tracking Control of a Robot With Flexible Joints, Journal of the Korean Society of Precision Engineering, 1992, p. 92-100.
Han-Sig Lee, The Prospects for the Future on Research of Flexible Automation and Robot System, 1992, p. 37-38.
Young Hood Joo, Seok Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.
H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.
Morris R. Driels, W. Swayze, S. Potter, Full-Pose Calibration of a Root Manipulator Using a Coordinate-Measuring Machine, The International Journal of Advanced Manufacturing Technology, 1993, p. 34-41.
M. Wu, B. C. Jiang, Y. R. Shiau, Controlling a Robot's Position Using Neural Networks, The International Journal of Advanced Manufacturing Technology, 1993, p. 216-226.
Joachim O. Berg, Path and Orientation Accuracy of Industrial Robots, The International Journal of Advanced Manufacturing Technology, 1993, p. 29-33.
Shaheen Ahmad, Mohamed Zribi, Lyapunov-Based Control Design for Multiple Robots Handling a Common Object, Dynamics and Control, 1993, p. 127-157.
S.D. Park, K.W. Jeong, W.K. Chung, Y. Youm, Development of a Control Method Using Both Electric and Pneumatic Actuators for a Heavy Load Handing Robot, Journal of the Korean Society of Precision Engineering, 1993, p. 14-21.
Nicolay V. Kim, Algorithms of Observation Information Synthesis, International Conference on Electronics, Informations and Communications, 1993, p. 120-124.
Sung Do Chi, Seok Pil Lee, Wang Jae Lee, San Hui Park, Hierarchical Design of Intelligent Robot System, Hankuk Aviation Univ., Yonsel Univ., 1993, p. 213-216.
Cai Zi-Xing, Jiang Zhiming, High-Level Expert System-Based Robot Planning, 1993.
Yong-Deuk Seo, Dong-Joon Choi, Ki-Sang Hong, Hong Joeng, The Development of Intelligent Robot Using Vision and Speech Recognition System, Department of EE, Postech, 1993, p. 39-44.
Jae-Hun Jung, Yong-Hyun Jung, Jong-Mo Kim, Suck-Gyu Lee, Dal-Hae Lee, Motion Control of Autonomous Mobile Robot With Fuzzy Algorithm, Yeungnam Univ., 1993, p. 362-365.
Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering, 1993, p. 170-177.
A Study on a Basic System Configuration for the PC Interface and the Robot Trajectory Generation, 1993, p. 354-358.
G.T. Yang, S.D. Ahn, S.C. Lee, Tip Position Control of Flexible Robot Arm by Self-Tuning Fuzzy Algorithm, Chonbuk Univ., 1993, p. 213-217.
Jeong Park, Hoe-Young Yoo, The Study of the Method of Position Control for the One-Link Flexible Robot Arm, 1993, p. 57-60.
Asea Industrial Robot System IRb-60, 1975, p. 1-8.
Robots Take a Hold on Production, 1982, p. 122-129.
M. Peter Heilburn, M.D., J., Preliminary Experience With Brown-Robert-Wells (BRW) Computerized Tomography Stereotaxis Guidance System, Neurourgery, 1983, p. 217-221.
International Machine Intelligence Robot System Users Manual, International Machine Intelligence, 1983.
Orbitran Wafer Handling Robot, Genmark Automation, 1989, p. 2,3,4.
H Kojima, R Toyama, Development of Wall Cleaning Robot, 1992.
International Search Report and Written Opinion dated Nov. 28, 2012, issued in related International Application No. PCT/US2012/040414.
International Search Report and Written Opinion dated Feb. 27, 2013, issued in related International Application No. PCT/US2012/054802.
International Search Report and Written Opinion dated Apr. 25, 2013, issued in related International Application No. PCT/US2012/070924.
International Search Report and Written Opinion dated May 31, 2012, issued in related International Application No. PCT/US2011/060214.
Australia Office Action dated Jun. 19, 2014, issued in related Australia Application No. 2011283048.
International Search Report and Written Opinion dated Dec. 9, 2013, issued in related International Application No. PCT/US2013/054326.
International Search Report and Written Opinion dated May 30, 2012, issued in related International Application No. PCT/US2011/057282.
Office Action and English summary from Japanese application 2013-521833 dated Mar. 24, 2015.
Office Action dated Dec. 27, 2015 issued in corresponding Japan Application No. 2013-521833, with English language summary.
Office Action issued in related Israeli Application No. 224420, dated Mar. 31, 2016 and English summary.
Extended European Search Report dated Oct. 31, 2016 issued in corresponding European Application No. 11812965.9.
Japanese Final Office Action dated Nov. 15, 2016 issued in corresponding Japanese Application No. 2013-521833, with English language summary.
Korean Office Action dated Aug. 30, 2017 issued in corresponding Korean Application No. 10-2013-7004589, with English language summary.
Australian Office Action dated Oct. 30, 2017 issued in corresponding Australian Application No. 2016202130.
Canadian Office action dated Oct. 26, 2017 issued in corresponding Canadian Application No. 2,806,278.

\* cited by examiner

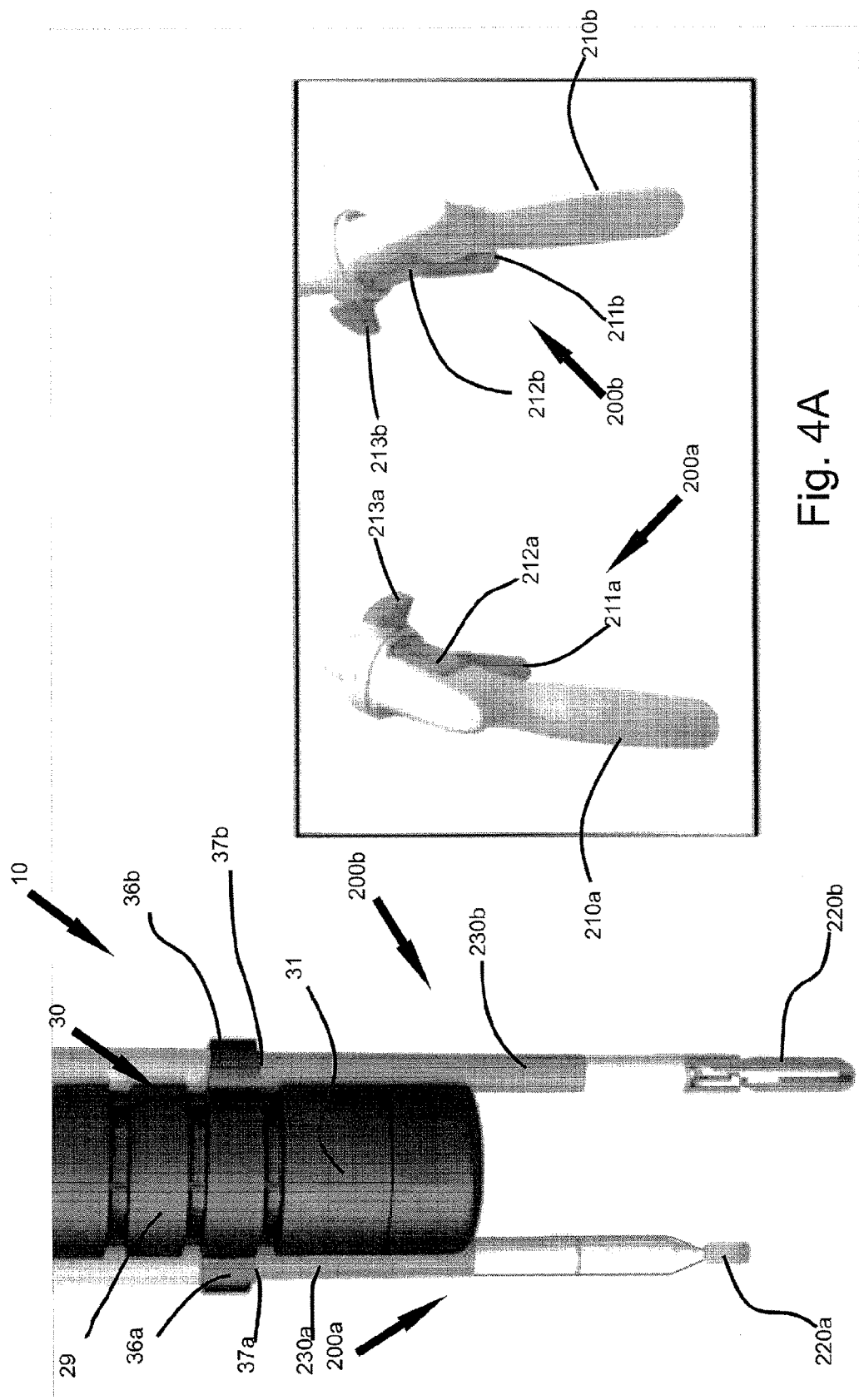

SURGICAL POSITIONING AND SUPPORT SYSTEM

RELATED APPLICATIONS

This application claims the benefit of U.S. Provisional Application Ser. No. 61/368,257 filed Jul. 28, 2010, which is incorporated herein by reference, in its entirety.

FIELD

Embodiments relate generally to the field of robotics and more particularly, to three dimensional, flexible, steerable robotic devices.

BACKGROUND

There are numerous types of steerable multi-linked probes, and such devices are utilized in a variety of different applications. Robert Sturges' U.S. Pat. No. 5,759,151, which is hereby incorporated by reference in its entirety, discloses a flexible, steerable device for conducting exploratory procedures. The device includes at least one spine, each having stiffening means for selectively rendering the spine rigid and flexible along its length. A flexible sheath surrounds the spine and is axially slidably moveable relative to the spine so that the sheath will follow and conform to the shape of a spine in the rigid state and resist further flexure when the spine is in a relaxed state. A steerable distal tip is provided on the distal end of the device. Controls for the distal tip are mounted on the proximal end of the device. Mechanisms are provided on the distal end of the device for selectively activating and deactivating the stiffening means of the spine. An instrument conduit may be mounted on the sheath. Howie Choset's U.S. patent application Ser. No. 11/630,279, which is hereby incorporated by reference in its entirety, discloses a feeder mechanism for advancing and retracting both an inner core and an outer sleeve, as well as selectively applying tension to control cables used for steering and causing either the inner core or outer sleeve to transition between a rigid state and a limp state.

U.S. Pat. No. 6,610,007 to Amir Belson, et. al., incorporated herein by reference in its entirety, discloses a steerable endoscope having an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body allowing it to negotiate tortuous curves along a desired path through or around and between organs within the body.

For medical use and other critical applications, it is extremely important that each device not only perform as intended and within known specifications, but have repeatable performance and otherwise consistent operation from use to use. For these and other reasons, there is a need for systems, devices and methods which provide integrated calibration routines and mechanisms.

SUMMARY

According to a first aspect, a system for performing a medical procedure, such as a TransOral Robotic Surgery (TORS) procedure, is disclosed. The system includes at least one tool comprising a proximal portion and a distal portion with a distal end. A tool support is configured to support the distal portion of the tool. A human interface device (HID) is used by an operator to manipulate the tool support. The human interface device produces control signals which are received by a controller which manipulates the tool support. In a preferred embodiment, the operator receives direct tactile feedback from the at least one tool. For example, during advancement, retraction, rotation or flexion, forces imparted on a distal portion of the tool are transmitted down the tool shaft to a handle held by the operator.

In one embodiment, the tool support comprises an inner core of links and an outer sleeve of links, each configured to transition between a limp state and a rigid state. In another embodiment, the tool support is malleable, or includes a malleable component, such as to be hand formed into a preferred shape. In another embodiment, the tool support is made rigid by one or more of: cables; temperature change; chemical change such as change to an epoxy, glue or cement, or combinations of these.

The tool support may include one or more guide holes or guide tubes configured to slidingly receive the shaft of one or more tools.

According to another aspect, a method of performing a medical procedure is disclosed.

In one aspect, a system for performing a medical procedure comprises: at least one tool comprising a proximal portion and a distal portion with a distal end; a tool support constructed and arranged to support the distal portion of the at least one tool; a human interface device constructed and arranged to create control signals based on operator input; and a controller constructed and arranged to receive the control signals and manipulate the tool support based on the received control signals.

In some embodiments, the system is constructed and arranged to perform a TORS procedure.

In some embodiments, the system is constructed and arranged to provide direct tactile feedback of forces encountered by the at least one tool.

In some embodiments, the forces are forces encountered during advancement or retraction of the at least one tool.

In some embodiments, the tool support comprises at least a malleable portion.

In some embodiments, the tool support comprises a highly articulated probe comprising at least a portion that is controllably rigid and flexible.

In some embodiments, the system further comprises at least one cable, wherein the tool support is constructed and arranged to transition between flexible and rigid when the at least one cable is tensioned.

In some embodiments, the tool support is constructed and arranged to transition between flexible and rigid by a temperature change.

In some embodiments, the tool support is constructed and arranged to transition between flexible and rigid by a chemical change.

In some embodiments, the system further comprises a substance selected from the group consisting of: an epoxy;

a cement; a glue; and combinations thereof, wherein the chemical change is a chemical change to said substance.

In some embodiments, the tool support comprises at least a rigid portion.

In some embodiments, the tool support comprises at least a flexible portion.

In some embodiments, the tool support further comprises at least a rigid portion.

In some embodiments, the tool support comprises a sleeve comprising a first set of links.

In some embodiments, the set of links comprises a distal portion and the distal portion comprises at least one guide hole.

In some embodiments, the system further comprises a guide tube.

In some embodiments, the tool support further comprises an inner core surrounded by the sleeve and comprising a second set of links.

In some embodiments, the at least one second set link is shorter than at least one first set link.

In some embodiments, the tool support further comprises at least one flange surrounding at least one link of the first set of links and the at least one flange comprises at least one guide hole.

In some embodiments, the flange comprises at least two guide holes.

In some embodiments, the tool support further comprises at least two flanges surrounding at least two links of the first set of links.

In some embodiments, a first flange has a geometry different than a second flange.

In some embodiments, the tool support comprises at least three flanges surrounding at least three links of the first set of links.

In some embodiments, the at least one flange is fixedly attached to the at least one link of the first set of links.

In some embodiments, the at least one flange is rotatably attached to the at least one link of the first set of links.

In some embodiments, the at least one flange is removably attached to the at least one link of the first set of links.

In some embodiments, the first set of links includes at least one guide hole.

In some embodiments, the system further comprises a guide tube positioned into or through the at least one guide hole.

In some embodiments, the first set of links includes at least two guide holes.

In some embodiments, a first guide hole is linearly aligned with a second guide hole. In some embodiments, a first guide hole is positioned approximately 180° from a second guide hole. In some embodiments, a first guide hole is positioned approximately 120° from a second guide hole.

In some embodiments, the system further comprises a camera lens positioned approximately 120° from the first guide hole and the second guide hole.

In some embodiments, the tool support comprises a distal portion comprising at least one guide hole.

In some embodiments, the system further comprises a guide tube comprising a lumen that is collinear with the at least one guide hole.

In some embodiments, the guide tube is constructed and arranged to be inserted into the guide hole.

In some embodiments, the guide tube is fixedly attached to the guide hole.

In some embodiments, the system further comprises at least one guide tube.

In some embodiments, the tool support comprises a distal portion and the at least one guide tube is attached to said distal portion.

In some embodiments, the at least one guide tube is removably attached to said distal portion.

In some embodiments, the system further comprises a tool support introducer wherein the at least one guide tube is attached to the tool support introducer.

In some embodiments, the at least one guide tube is removably attached to the tool support introducer.

In some embodiments, the at least one guide tube comprises at least one flexible portion.

In some embodiments, the at least one guide tube comprises at least one rigid portion.

In some embodiments, the at least one guide tube comprises at least one flexible portion and at least one rigid portion.

In some embodiments, the tool support comprises a distal portion comprising a distal end.

In some embodiments, the distal portion comprises a distal link.

In some embodiments, the distal link is constructed and arranged to be rotated.

In some embodiments, the distal portion further comprises a camera component selected from the group consisting of: a camera such as a CCD; a lens; a fiber optic; and combinations thereof.

In some embodiments, the camera component comprises a center and said center is positioned off center from a central axis of the distal portion.

In some embodiments, the distal end comprises a diameter and said camera component center is positioned at least 25% of the diameter from the central axis.

In some embodiments, the system further comprises a guide hole wherein the camera component is constructed and arranged to move in synchrony with an axis of the guide hole.

In some embodiments, the distal portion further comprises at least one light element.

In some embodiments, the at least one light element comprises at least one LED.

In some embodiments, the at least one light element is constructed and arranged to emit one or more of: visible light; infrared light; and ultraviolet.

In some embodiments, the distal portion further comprises at least one tool channel and exit hole.

In some embodiments, the tool support comprises an outer sleeve and an inner core, and wherein the tool channel extends proximally between the outer sleeve and the inner core.

In some embodiments, the at least one tool channel is constructed and arranged to supply a tool to the distal end of the tool support.

In some embodiments, the distal end is constructed and arranged to minimize reflections of visible light.

In some embodiments, the distal end comprises a matte surface.

In some embodiments, the distal end comprises a dark color.

In some embodiments, the distal end comprises a color approximating black.

In some embodiments, the distal portion comprises at least one recess along its length.

In some embodiments, the at least one tool comprise a shaft and wherein the recess is constructed and arranged to allow said shaft to pass therethrough.

In some embodiments, the tool support comprises a highly articulated probe, comprising: an outer sleeve comprising a first plurality of links; an inner core comprising a second plurality of links; a first cable extending through either said plurality of links of the inner core or said plurality of links of the outer sleeve and a plurality of cables running through the other of said plurality of links of the inner core or said plurality of links of the outer sleeve.

In some embodiments, the system further comprises a feeder assembly constructed and arranged to alternate each of said inner core and outer sleeve between a limp mode and a rigid mode, for advancing and retracting said inner core and outer sleeve, and for steering at least one of said inner core and outer sleeve.

In some embodiments, the controller comprises a CPU.

In some embodiments, the controller comprises a cable tensioning assembly.

In some embodiments, the controller comprises a temperature modifying assembly.

In some embodiments, the controller comprises a delivery device.

In some embodiments, the controller is constructed and arranged to deliver one or more of: epoxy; cement; and glue.

In some embodiments, the at least one tool comprises a handle attached to the at least one tool proximal portion.

In some embodiments, the handle comprises a control.

In some embodiments, the control is selected from the group consisting of: a trigger; a knob; a lever; a button; a lock; and combinations thereof.

In some embodiments, the control is constructed and arranged to perform one or more of the following actions; operate the at least one tool such as to apply power to the at least one tool; and move a potion of the at least one tool such as to advance, retract or rotate a portion of the tool.

In some embodiments, the at least one tool distal portion comprises a functional element.

In some embodiments, the functional element is selected from the group consisting of: grasper; cutter; ablater; cauterizer; drug delivery element; radiation source; sensor such as an EKG electrode, pressure sensor or blood sensor; magnet; heating element; cryogenic element; and combinations thereof.

In some embodiments, the at least one tool distal portion is a steerable.

In some embodiments, the at least one tool comprises a rigid portion proximal said steerable tool distal portion.

In some embodiments, the at least one tool comprises a flexible portion proximal said rigid portion.

In some embodiments, the at least one tool comprises a flexible portion proximal said steerable tool distal portion.

In some embodiments, the at least one tool comprises a rigid portion proximal said tool flexible portion.

In some embodiments, the at least one tool comprises a rigid portion between said tool steerable portion and said tool flexible portion.

In some embodiments, the system further comprises a tool holder constructed and arranged to attach to the at least one tool proximal portion.

In some embodiments, the tool holder comprises mounting means.

In some embodiments, the mounting means is configured to rapidly release.

In some embodiments, the mounting means is configured to rapidly rotate.

In some embodiments, the tool holder is constructed and arranged to operably position the at least one tool.

In some embodiments, the tool holder is constructed and arranged to allow the distal portion to advance and/or retract when the at least one tool is attached to the tool holder.

In some embodiments, the tool holder is constructed and arranged to allow the distal portion to rotate when the at least one tool is attached to the tool holder.

In some embodiments, the tool holder is constructed and arranged to prevent movement of at least a portion of the at least one tool when the at least one tool is attached to the tool holder.

In some embodiments, the human interface device is constructed and arranged to simultaneously advance and steer the tool support.

In some embodiments, the tool support comprises an outer sleeve comprising a first set of links and an inner core comprises a second set of links.

In some embodiments, the system is constructed and arranged to advance and steer the outer sleeve simultaneously based on input from the human interface device.

In some embodiments, the outer sleeve comprises a distal end and the inner core comprises a distal end and wherein the system is constructed and arranged to advance the outer sleeve distal end up to approximately 2.5 cm beyond the inner core distal end.

In some embodiments, the system is constructed and arranged to advance the inner core distal end up to the outer sleeve distal end without operator input after the outer sleeve has been simultaneously advanced and steered.

In some embodiments, the human interface device comprises a haptic controller.

In some embodiments, the system further comprises a console.

In some embodiments, the human interface device is attached and/or integral to the console.

In some embodiments, the console comprises a user interface.

In some embodiments, the system further comprises a second tool comprising a proximal portion and a distal portion with a distal end.

In some embodiments, the tool support is further constructed and arranged to support the second tool distal portion.

In some embodiments, the system further comprises a tool support introducer comprises a tube constructed and arranged to slidingly receive the tool support.

In some embodiments, the tool support introducer is constructed and arranged for insertion into the esophagus.

In some embodiments, the tool support introducer further comprises at least one guide tube.

In some embodiments, the at least one guide tube comprises a rotatable coupler along its length.

In some embodiments, the rotatable coupler is constructed and arranged to frictionally engage and gravitationally support the at least one guide tube.

In some embodiments, the rotatable coupler is constructed and arranged to lock the at least one guide tube such that movement is prevented when a force is applied to the at least one guide tube.

In some embodiments, the rotatable coupler comprises a cam lock.

In some embodiments, the cam is operably attached to a lever.

In some embodiments, the at least one guide tube comprises a flared proximal end.

In some embodiments, the tool support tube comprises at least one radially extending side lobe.

In some embodiments, the tool support comprises a proximal end comprising two or more projections constructed and arranged to guide and/or orient insertion of the tool support.

In some embodiments, the tool support tube comprises a proximal portion and a distal portion.

In some embodiments, the tool support further comprises a second proximal portion different than the first proximal portion.

In some embodiments, the tool support further comprises a second distal portion different than the first distal portion.

In some embodiments, the tool support introducer further comprises an attachment mechanism.

In some embodiments, the system further comprises an intubation tube.

In some embodiments, the tool support is constructed and arranged to be positioned anterior to the intubation tube in the esophagus.

In some embodiments, the operator is a clinician.

In some embodiments, the clinician is a surgeon.

In another aspect, a method of performing a surgical procedure comprises: selecting the system of any embodiments described herein; and manipulating the tool support to position the at least one tool.

In some embodiments, the method further comprises placing the tool support in a curvilinear configuration and transitioning the tool support to a rigid state.

In some embodiments, transitioning the tool support to a rigid state comprises placing one or more cables in tension.

In some embodiments, transitioning the tool support to a rigid state comprises freezing at least a portion of the tool support.

In some embodiments, transitioning the tool support to a rigid state comprises hardening one or more of: cement; epoxy; glue; and combinations thereof.

In some embodiments in a system as described in reference to the figures, the tool shafts exit the patient's mouth and travel in a superior direction.

In some embodiments in a system as described in reference to the figures, the tool support shaft exits the patient's mouth and does not travel in a superior direction.

In some embodiments in a system as described in reference to the figures, the tool support shaft exits the patient's mouth and travels in an inferior direction.

In another aspect, a tool support is described in reference to the embodiments described herein.

In another aspect, a method of performing a medical procedure is described in reference to the system of any of the embodiments described herein.

BRIEF DESCRIPTION OF THE DRAWINGS

The accompanying drawings, which are incorporated in and constitute a part of this specification, illustrate various embodiments of the present inventive concepts, and together with the description, serve to explain the principles of the inventive concepts. In the drawings:

FIG. 4 illustrates a side view of the distal end of a tool support and the distal portions of two tools, in accordance with the present inventive concepts;

FIG. 4A illustrates a perspective view of handles of the two tools of FIG. 4, in accordance with the present inventive concepts;

FIG. 6A illustrates a perspective view of the handles of FIG. 5;

FIG. 9A illustrates a side view of the tool of FIG. 9 with a distal portion manipulated to a curvilinear configuration, in accordance with the present inventive concepts;

DETAILED DESCRIPTION OF EMBODIMENTS

Reference will now be made in detail to the present embodiments of the invention, examples of which are illustrated in the accompanying drawings. Wherever possible, the same reference numbers will be used throughout the drawings to refer to the same or like parts.

Provided herein is a system for performing a medical procedure including one or more tools that are operably attached to a tool support. An operator, such as a clinician, operates a human interface device (HID) to manipulate or otherwise control the tool support. A controller receives signals from the HID and controls the tool support based on these signals.

Figure 1:
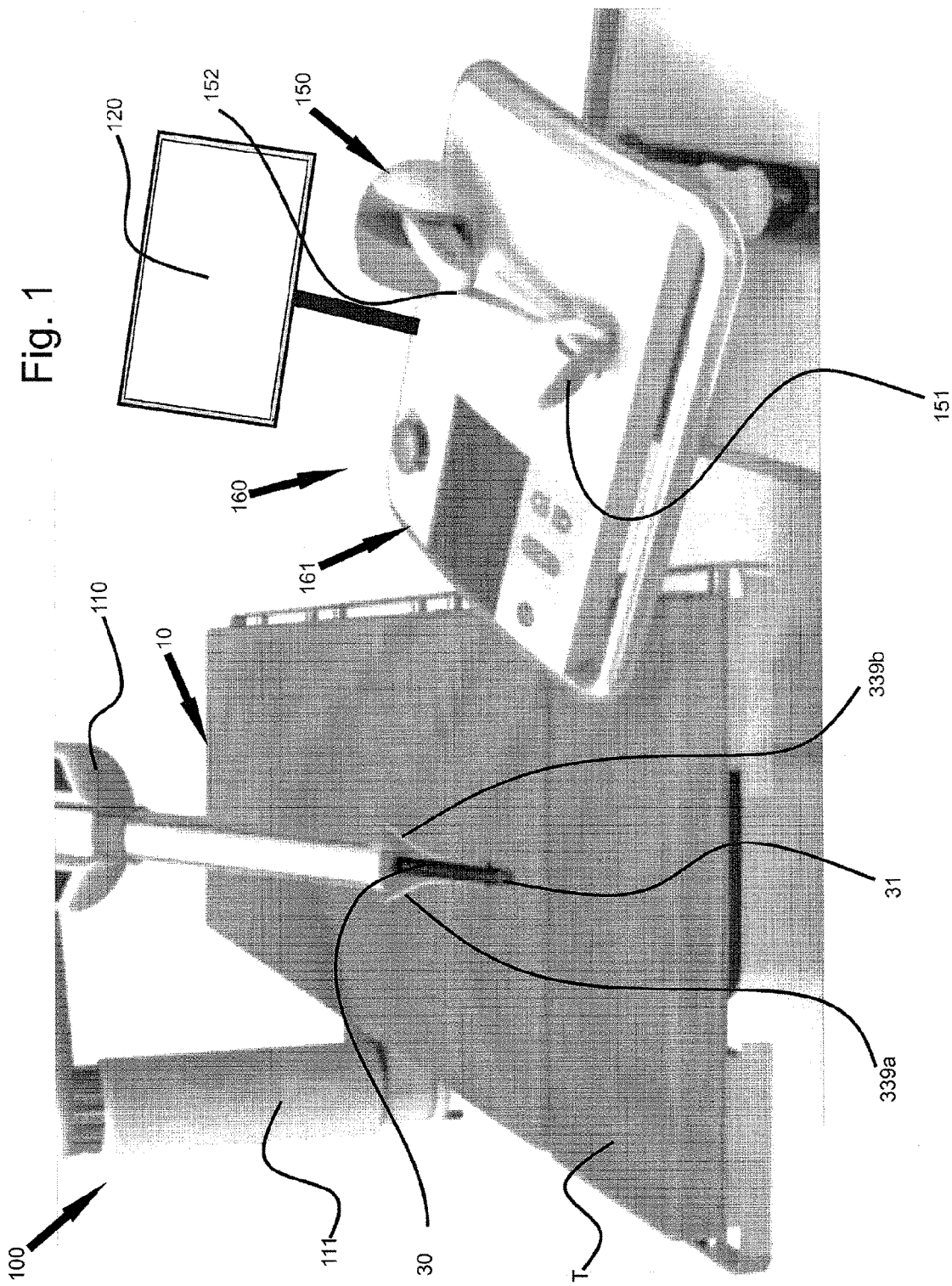
FIG. 1 illustrates a perspective view of a system for performing a medical procedure, in accordance with the present inventive concepts.

Referring now to FIG. 1, a system in accordance with the present inventive concepts is illustrated, with the patient removed for clarity. System 100 comprises probe 10, such as a highly articulated probe described in U.S. patent application Ser. No. 11/630,279 titled STEERABLE, FOLLOW THE LEADER DEVICE, or U.S. patent application Ser. No. 11/838,519 titled STEERABLE MULTI LINKED DEVICE HAVING MULTIPLE WORKING PORTS, both incorporated by reference in their entirety herein. Probe 10, an exemplary tool support of the present invention, comprises feeder 110 which controllably advances one or more cables within outer sleeve 30 of probe 10, such as a cable, not shown, but extending to distal link 31. System 100 further comprises console 160 which includes user interface 161, monitor 120, and HID 150. Monitor 120 may be used to display output of a camera, such as a camera integral to distal link 31 of probe 10.

HID 150, typically a haptic controller, joystick, track ball, mouse, or other control device known to those of skill in the art of robotics or other electromechanical device control. HID 150 includes handle 151 configured to manipulate distal end 31 of probe 10.

Outer sleeve 30 includes near its distal end, guide tube 339a and guide tube 339b, each including at least one lumen, not shown, but configured to slidingly receive the distal portion of one or more tools, also not shown but described in detail herebelow. Guide tubes 339a and 339b may be flexible, rigid, or include flexible and rigid portions.

Feeder 110 is mounted to table T via support 111. Alternatively or additionally, feeder 110 may be mounted to console 160 or a separate support device.

Figure 2:
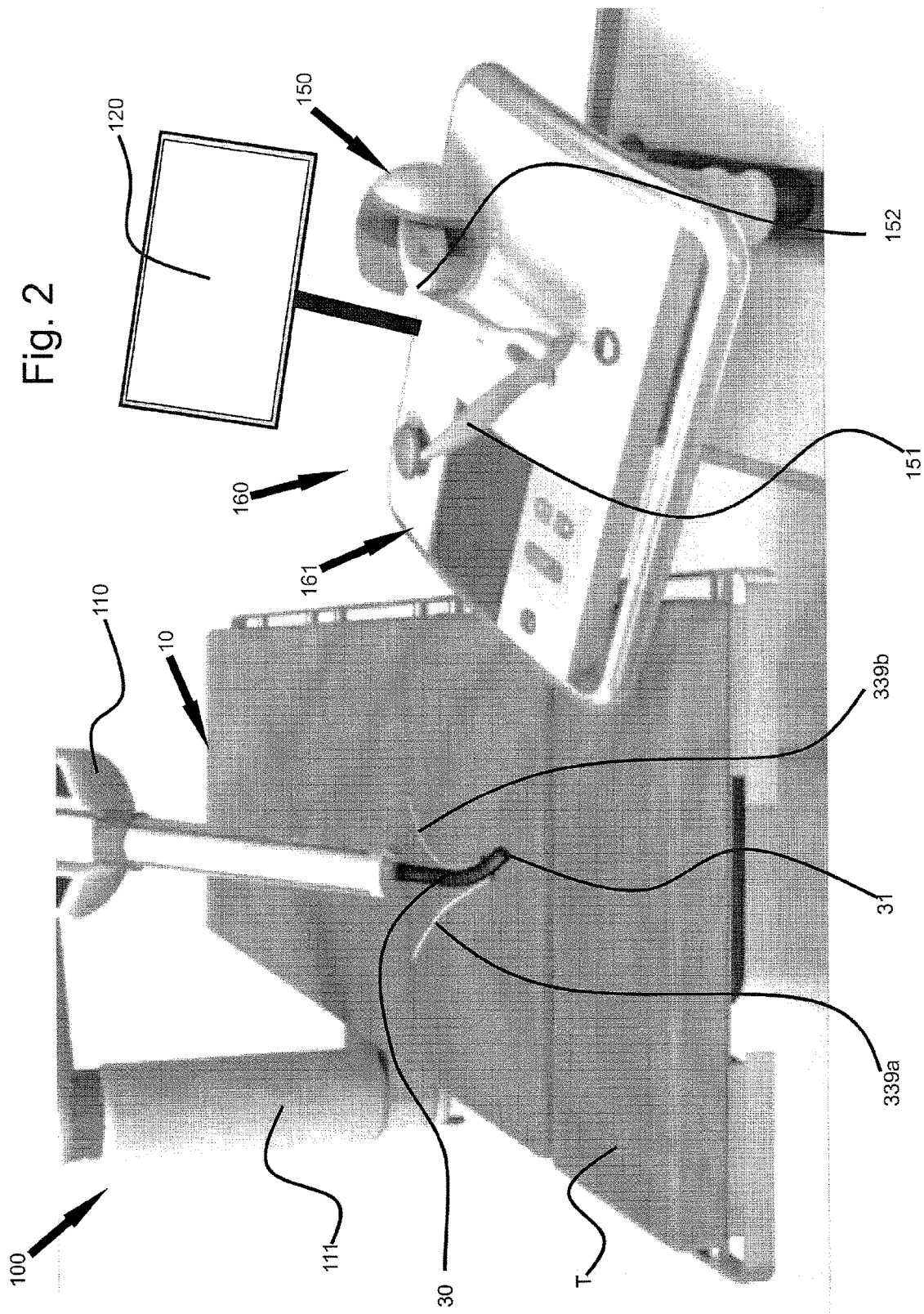
FIG. 2 illustrates a perspective view of the system of FIG. 1 with a tool support in a curvilinear configuration, in accordance with the present inventive concepts.

Referring now to FIG. 2, system 100 of FIG. 1 is illustrated with the outer sleeve 30 flexed toward the right of the page, such as via manipulation of handle 151 of HID 150 to the left of the page, as shown. In an alternative embodiment, handle 151 is manipulated to the right to cause outer sleeve 30 to flex to the right. Other manipulations of handle 151 (e.g. rotating, pulling or pushing, and twisting) and manipulations of other portions or components of HID 150 can be used to advance or retract outer sleeve 30, rotate or flex sleeve 30, activate one or more functional elements of sleeve 30 or probe 10, and the like.

Figure 3:
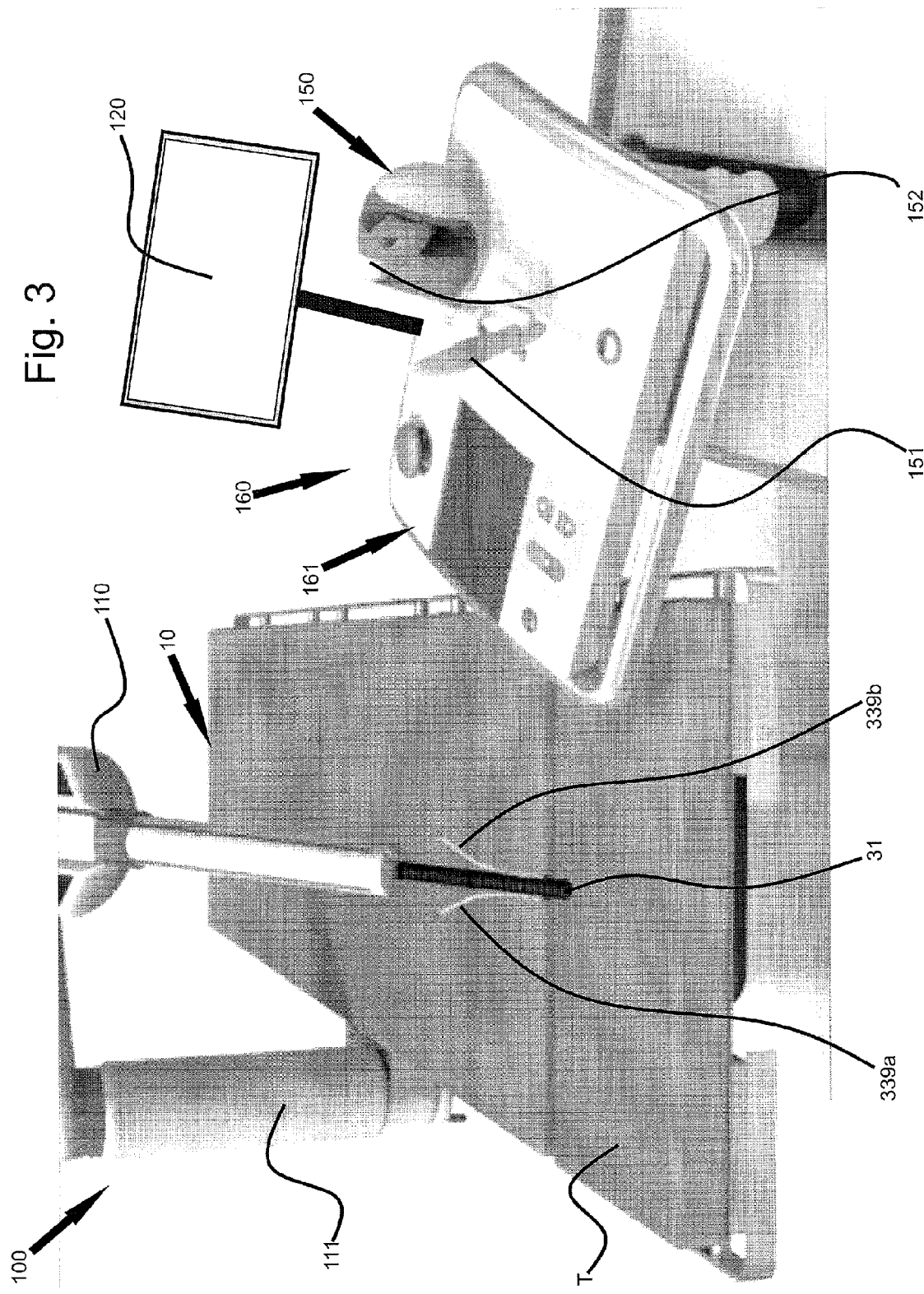
FIG. 3 illustrates a perspective view of the system of FIG. 1 with a tool support advanced, in accordance with the present inventive concepts.

Referring now to FIG. 3, system 100 of FIG. 1 is illustrated with the outer sleeve 30 and distal end 31 advanced forward, such as via manipulation of handle 151 HID 150 forward, bending elbow 152, as shown.

Referring now to FIG. 4, a tool support of the present disclosure is illustrated supporting two tools, with the patient removed for clarity. Probe 10 includes outer sleeve 30 comprising a plurality of outer links 29. At the distal end of sleeve 30 is distal link 31 which typically includes a camera, lighting elements and exits for one or more tool channels, all not shown, but described in detail herebelow. Outer sleeve 30 further includes flanges 36a and 36b which comprise guide holes 37a and 37b, respectively. Tool shaft 230a of tool 200a has been passed through guide hole 37a and tool shaft 230b of tool 200b has been passed through guide hole 37b. Located on the distal end of tool 200a is a functional element, working end 220a. Located on the distal end of tool 200b is another functional element, working end 220b. Functional elements are typically selected from the group consisting of: grasper; cutter; ablater; cauterizer; drug delivery element; radiation source; sensor such as an EKG electrode, pressure sensor or blood sensor; magnet; heating element; cryogenic element; and combinations of these. Referring additionally to FIG. 4A, handle 210a of tool 200a and handle 210b of tool 200b are illustrated. Handles 210a and 210b may include one or more controls, such as triggers; knobs; levers; buttons; locks; and combinations of these. As illustrated, handles 210a and 210b include triggers 211a and 211b, respectively, such as a trigger to actuate, deploy or otherwise control the working elements 220a and 220b, respectively. Handles 210a and 210b include rotating knobs 212a and 212b, respectively, such as knobs configured to rotate shafts 230a and 230b, respectively. Handles 210a and 210b include locking levers 213a and 213b, respectively, such as levers configured to lock one or more movable portions of tools 200a and 200b. Handles 210a and 210b include pivot joints 214a and 214b, respectively, which are configured to allow handles 210a and 210b to flex such as to flex shafts 230a and 230b, respectively.

Figures 5, 5A:
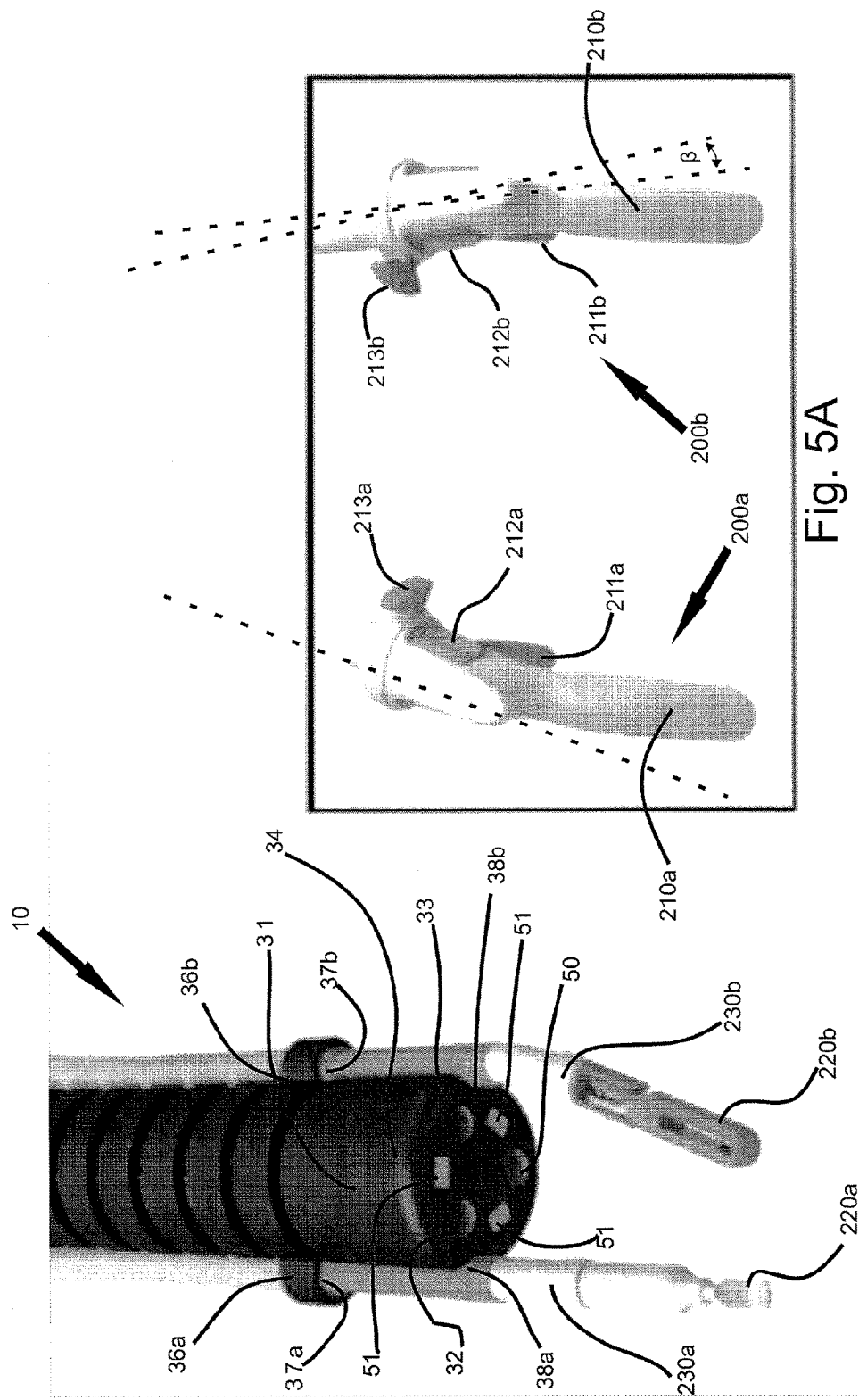
FIG. 5 illustrates a perspective view of the distal end of the tool support and tools of FIG. 4, in accordance with the present inventive concepts.
FIG. 5A illustrates a perspective view of the handles of FIG. 5.

Referring now to FIGS. 5 and 5A, probe 10 of FIGS. 4 and 4A is illustrated with the distal portion of tool 200b flexed toward the left of the page, such as by rotating handle 210b left an angle β. Shaft 230b and working portion 220b have been rotated, such as by rotating knob 212b. Lock 213b has been engaged such that shaft 230b will maintain the flexed position shown in FIG. 5.

Also as shown in FIG. 5, distal link 31 includes camera 50 positioned toward the bottom of distal link 31, as shown on the page. At 120° separation from camera 50 are channels 32 and 33, preferably working lumens or ports, such as those described in reference to U.S. patent application Ser. No. 11/838,519, titled STEERABLE MULTI LINKED DEVICE HAVING MULTIPLE WORKING PORTS, incorporated herein by reference, in its entirety, and extending proximally to the proximal end of probe 10 such that one or more devices can be inserted therethrough. In a particular embodiment, channels 32 and/or 33 are used as a flush port, such as to improve an image provided by camera 50. Distal link 31 further includes light elements, LEDs 51, typically visible light devices, but alternatively or additionally infrared or ultraviolet sources used to enhance or create an image from camera 50.

Distal link 31 also includes recesses 38a and 38b which allow shafts 230a and 230b of tools 200a and 200b, respectively, to pass therethrough. Distal link 31 is provided with a chamfered or rounded edge 34 such as to avoid trauma to tissue during insertion into the human body.

Distal link 31 can be constructed to minimize reflections of visible light, for example, distal link 31 can be a matte material and/or a dark color, such as black.

Figure 6:
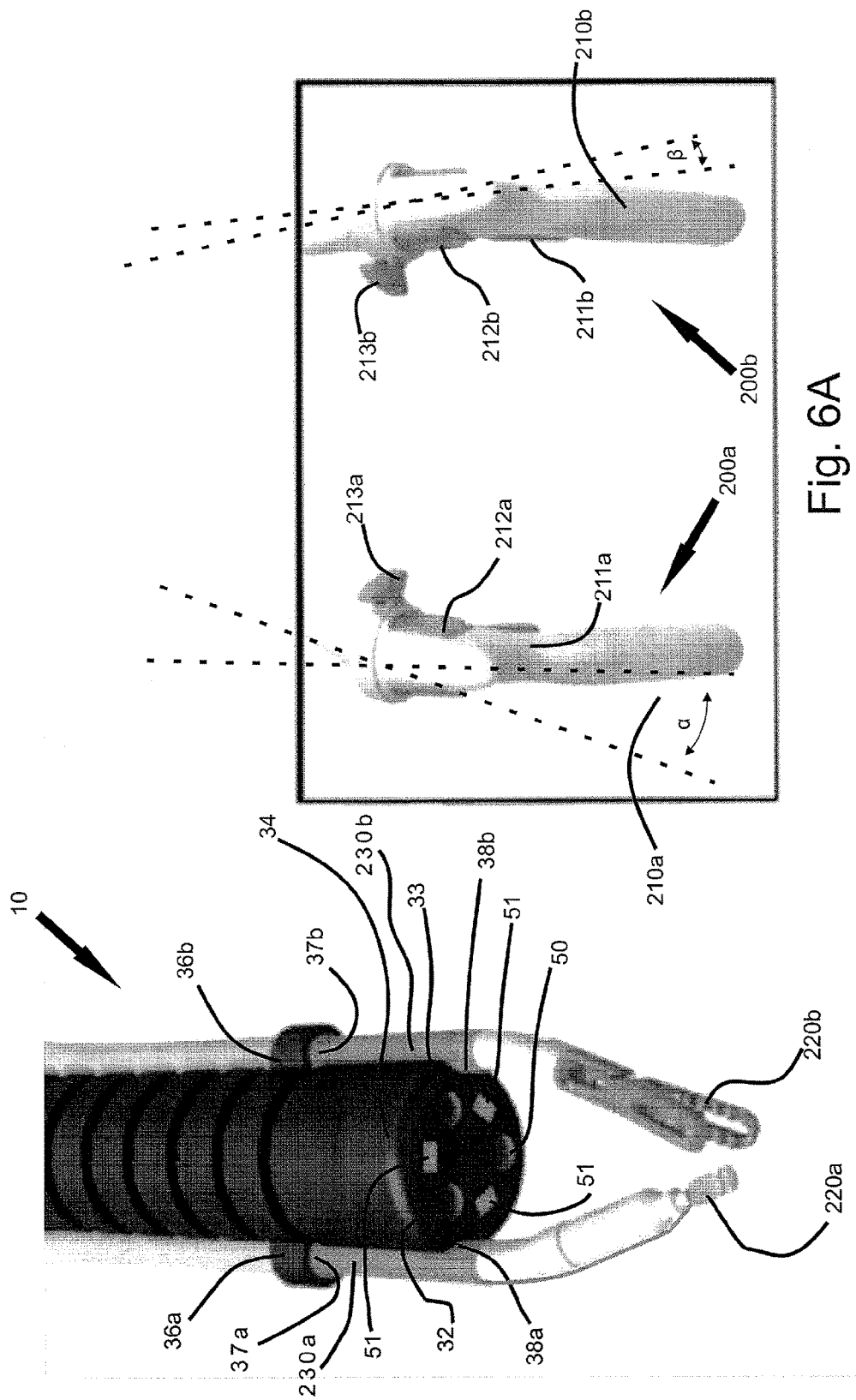
FIG. 6 illustrates a perspective view of the distal end of the tool support and tools of FIG. 4, in accordance with the present inventive concepts.

Referring now to FIGS. 6 and 6A, probe 10 of FIGS. 5 and 5A is illustrated with the distal portion of tool 200a flexed toward the right of the page, such as by rotating handle 210a right at angle α. Lock 213a has been engaged such that shaft 230a will maintain the flexed position shown in FIG. 6.

Figure 7:
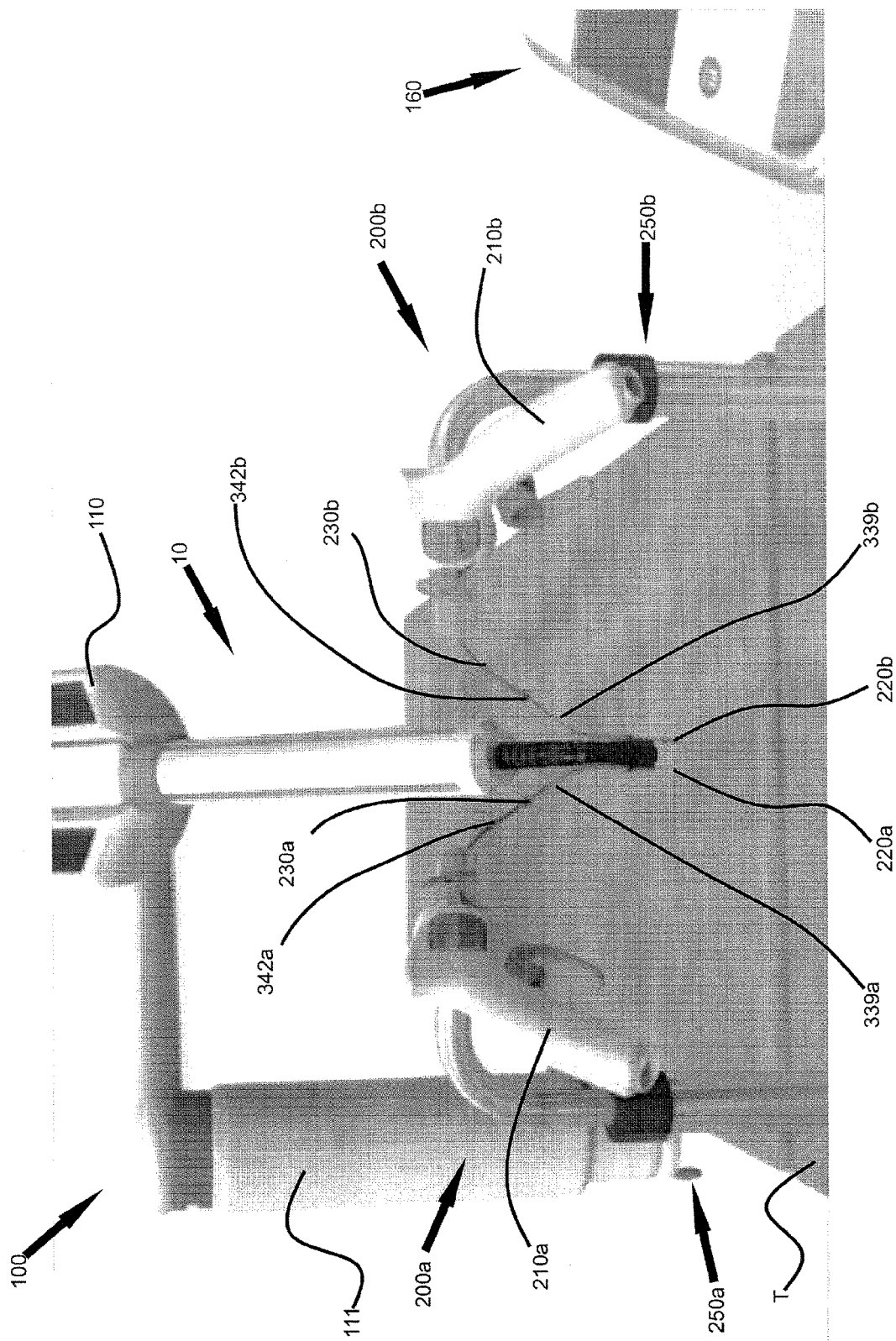
FIG. 7 illustrates a perspective view of a system for performing a medical procedure, in accordance with the present inventive concepts.

Referring now to FIG. 7, a system in accordance with the present inventive concepts is illustrated including two tools and a tool support, patient not shown for clarity. System 100 includes feeder 110 which is fixedly attached to support 111, attached to table T. Probe 10 is positioned and configured as has been described in detail hereabove, and is operably attached to console 160, attachment not shown but typically a conduit including electrical wires, fiber optic cables, fluid tubing (e.g. for flushing or hydraulic/pneumatics), mechanical linkages, and the like. Tool 200a and tool 200b are shown operably attached to tool holder 250a and tool holder 250b, respectively. Tools 200a and 200b include handles 210a and 210b, respectively. Tools shafts 230a and 230b extend from handles 210*a* and 210*b*, respectively. Tool shafts 230*a* and 230*b* have been inserted into funnels 342*a* and 342*b*, respectively, of guide tubes 339*a* and 339*b*, respectively. Guide tubes 339*a* and 339*b* each include a guide hole, as described herein, typically a lumen extending from one end to the other of guide tubes 339*a* and 339*b*, sized to accommodate the working portions 220*a* and 220*b*, and associated shafts 230*a* and 230*b* of tools 200*a* and 200*b*.

Figure 8:
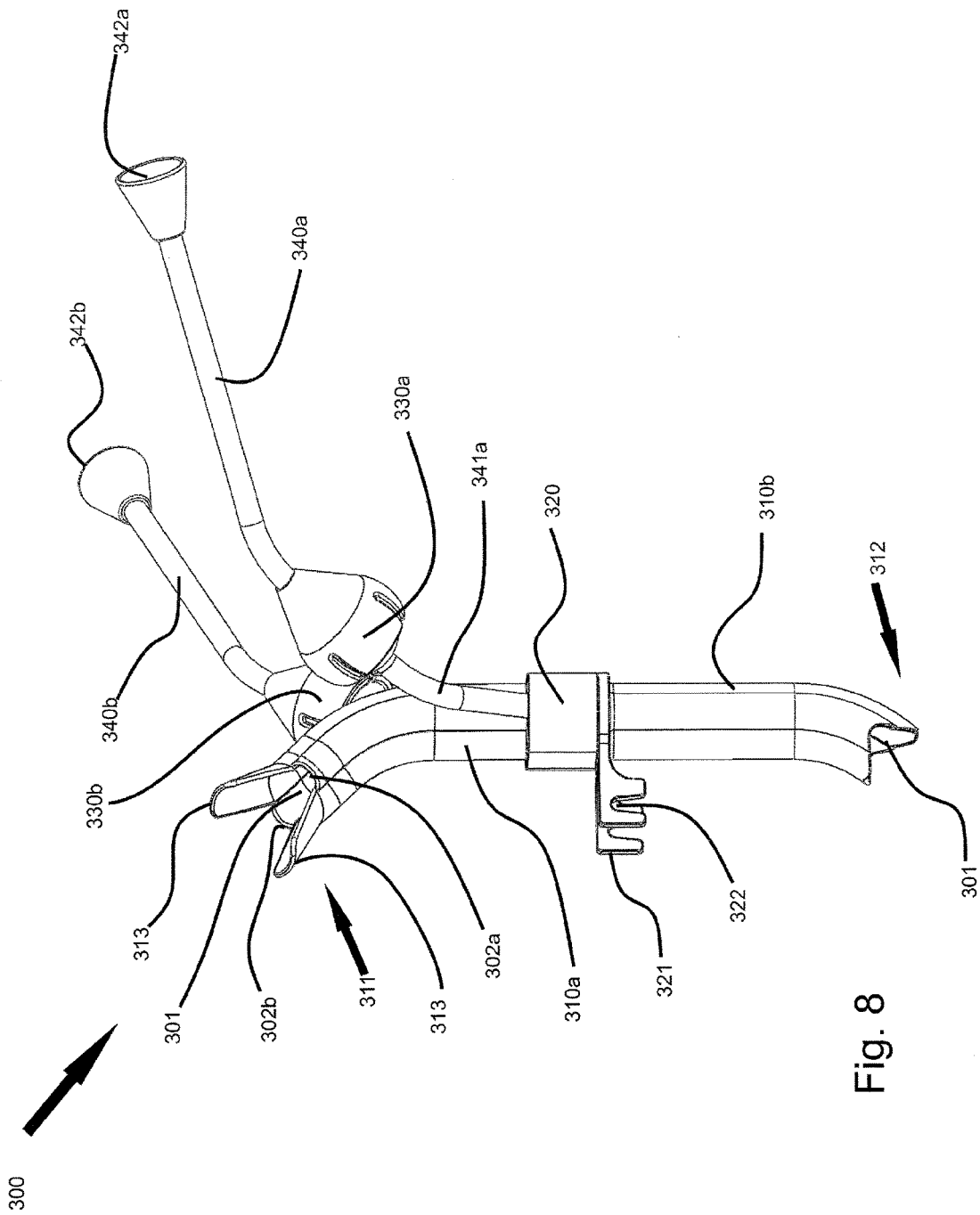
FIG. 8 illustrates a perspective view of a tool support introducer, in accordance with the present inventive concepts.

Referring now to FIG. 8, a tool support introducer in accordance with the present inventive concepts is illustrated. Introducer 300 includes a shaft comprising upper portion 310*a* which is attachable to lower portion 310*b* via coupler 320. Coupler 320 comprises bracket 321 which includes slot 322 positioned and sized to fit over a device such as a retractor placed in the patient's mouth.

Introducer 300 includes lumen 301 extending from its proximal end 311 to its distal end 312. Lumen 301 is sized to slidingly receive a tool support of the present disclosure, such as probe 10 of FIG. 1. Proximal end 311 includes projections 313 which are sized and positioned to orient a tool support, such as a tool support including radially extending flanges, such as probe 10 of FIG. 4. Introducer 300 includes radially extending side lobes 302*a* and 302*b*, which are sized and positioned to slidingly receive a radially extending member, such as the radially extending flanges of probe 10 of FIG. 4.

Introducer 300 includes two guide tubes comprising proximal portions 340*a* and 340*b*, and distal portions 341*a* and 341*b* (not shown but located behind upper shaft 310*a*), connected with rotating couplers 330*a* and 330*b*, respectively. Rotatable couplers 330*a* and 330*b*, typically frictionally engaged ball joints configured to provide gravitational support, may be detachable. Rotatable couplers 330*a* and 330*b* frictionally engage the guide tubes such that guide tube proximal portions 340*a* and 340*b* are supported and free to move relative to the rotation means within coupler 330*a* and 330*b*, respectively. Rotatable couplers 330*a* and 330*b* can be locked once the guide tubes are in a desired position and orientation relative to the user. In a locked state, couplers 330*a* and 330*b* prevent movement of the guide tubes when a force is applied, such as a force applied during manipulation of a tool. Funnels 342*a* and 342*b* are configured to ease insertion of the distal portion of one or more tools, and are attached to guide tube proximal portions 340*a* and 340*b*, respectively.

Figure 9:
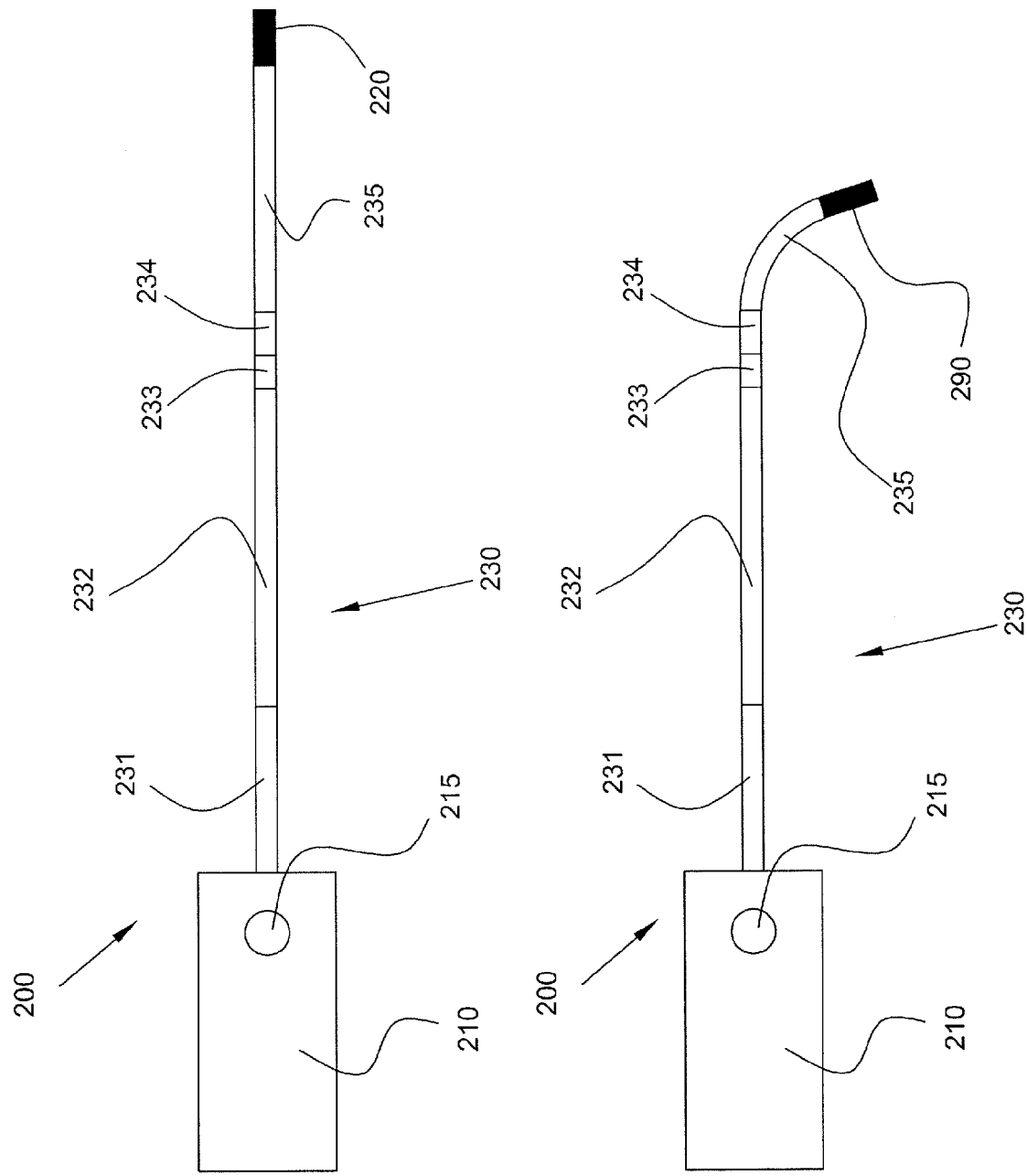
FIG. 9 illustrates a side view of a tool, in accordance with the present inventive concepts.

Referring now to FIG. 9, a tool in accordance with the present inventive concepts is illustrated. Tool 200 includes handle 210 which includes control 215, typically a button, lever, switch, knob, trigger, and the like. Extending from handle 210 is shaft 230, shown in a relatively linear orientation, which comprises a rigid portion 231, a flexible portion 232, a second rigid portion 233, a pivot point 234, and a distal portion 235, typically a flexible portion. Distal portion 235 includes working end 220, such as has been described in detail hereabove. Referring now to FIG. 9A, distal portion 235 has been rotated about pivot point 234, such as via rotation or other form of activation of control 215 of handle 210.

Figure 10:
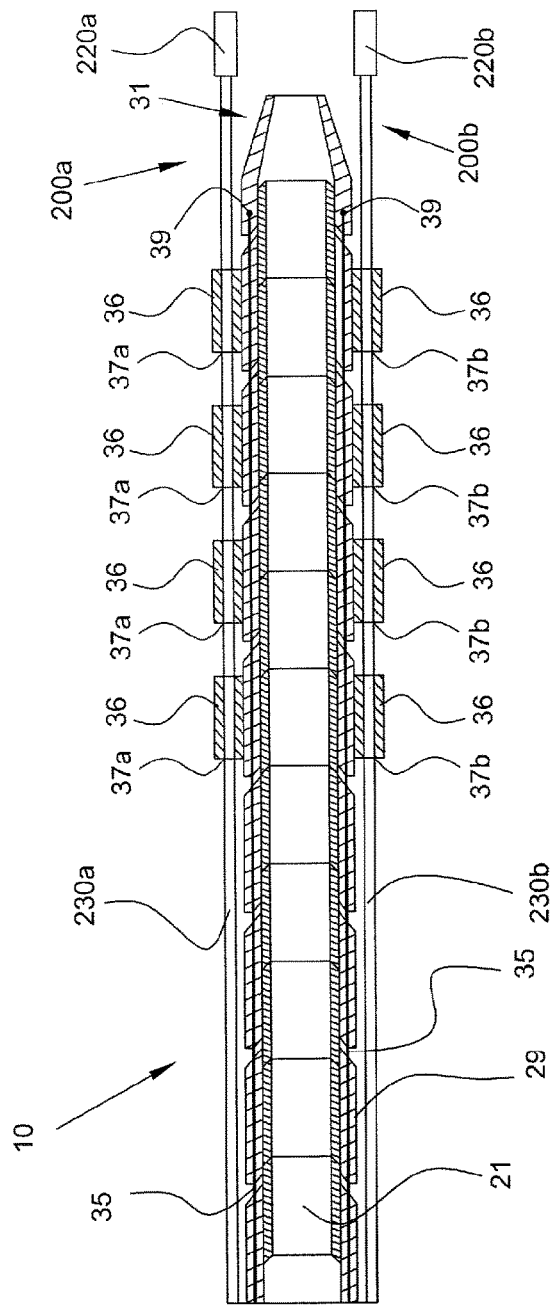
FIG. 10 illustrates a side sectional view of a tool support and two tools, in accordance with the present inventive concepts.

Referring now to FIG. 10, a sectional view of a tool support in accordance with the present inventive concepts is illustrated. Probe 10 comprises an inner core comprising a set of inner links 21, and an outer sleeve comprising a set of outer links 29. Near the distal portion of probe 10, multiple flanges 36 surround outer links 29. One or more flanges 36 may be attachable and/or detachable to or from outer links 29, and/or they may be permanently attached. Flanges 36 may be configured to rotate about outer links 29. At the distal end of probe 10 is distal link 31. One or more cables passes through a lumen and/or wall of inner link 21, cable not shown but described in detail in reference to U.S. patent application Ser. No. 11/630,279 titled "STEERABLE FOLLOW THE LEADER DEVICE", incorporated herein by reference, in its entirety. Typically three cables 35 (two shown) pass through the walls of outer links 29 and terminate at fixation point 39 within distal link 31. Movement of the inner cables or outer cables 35 can be used to bend probe 10 and make the inner and outer sleeve rigid, respectively.

Tools 200*a* and 200*b* include shafts 230*a* and 230*b*, respectively, which have been inserted through guide holes 37*a* and 37*b* of flanges 36. Tools 200*a* and 200*b* include working ends 220*a* and 220*b*, respectively.

Figure 10A:
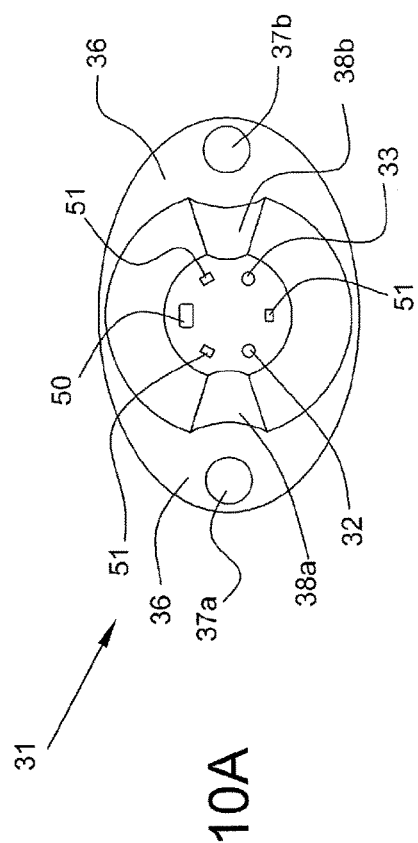
FIG. 10A illustrates an end view of the distal end of the tool support of FIG. 10, in accordance with the present inventive concepts.

Referring now to FIG. 10A, an end view of the probe of FIG. 10 is illustrated. Distal link 31 includes camera 50, LEDS 51, channel 32, channel 33, and recess 38*a* and recess 38*b*, as has been described hereabove. Also shown is flange 36 which includes guide holes 37*a* and 37*b*. In one embodiment, guide holes 37*a* and 37*b* are spaced 180° apart. In an alternate embodiment, guide holes 37*a* and 37*b* are spaced 120° apart.

Figure 11:
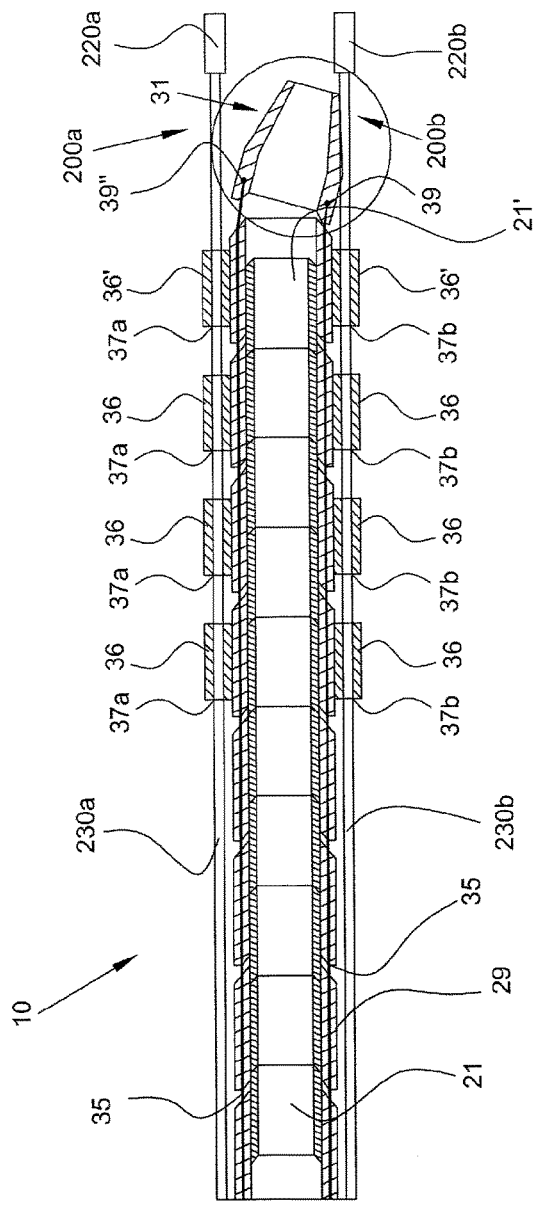
FIG. 11 illustrates a side sectional view of a tool support and two tools, in accordance with the present inventive concepts.
Figure 11A:
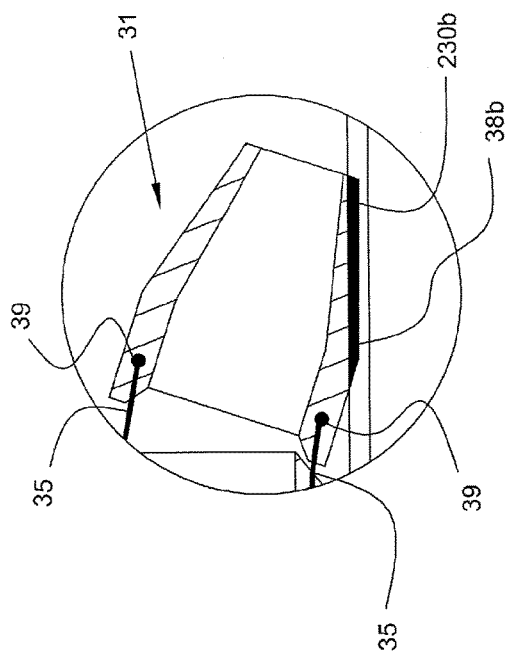
FIG. 11A illustrates a side sectional view of the distal end of the tool support of FIG. 10, in accordance with the present inventive concepts.

Referring now to FIG. 11, a sectional view of the tool support of FIG. 10 is illustrated with the inner core retracted with its distal link just proximal to the distal link of the outer sleeve. Distal most inner link 21' has been retracted, such as via one or more cables, not shown but controlled by a controller of the present invention, such that no portion of inner link 21' is within distal link 31. Cable 39' has been retracted such that distal link 31 pivots toward the bottom of the page (cable 39" may be simultaneously advanced to support the rotation). Since distal flange 36' has not rotated, working ends 220*a* and 220*b* of tools 200*a* and 200*b* remain as positioned in FIG. 10. Camera 50, not shown but described in reference to FIG. 10*a*, has its viewing window moved proportional with the movement of distal link 31. As shown in FIG. 11*a*, as distal link 31 is pivoted, tool shaft 230*b* enters recess 38*b* of distal link 31.

Figure 12:
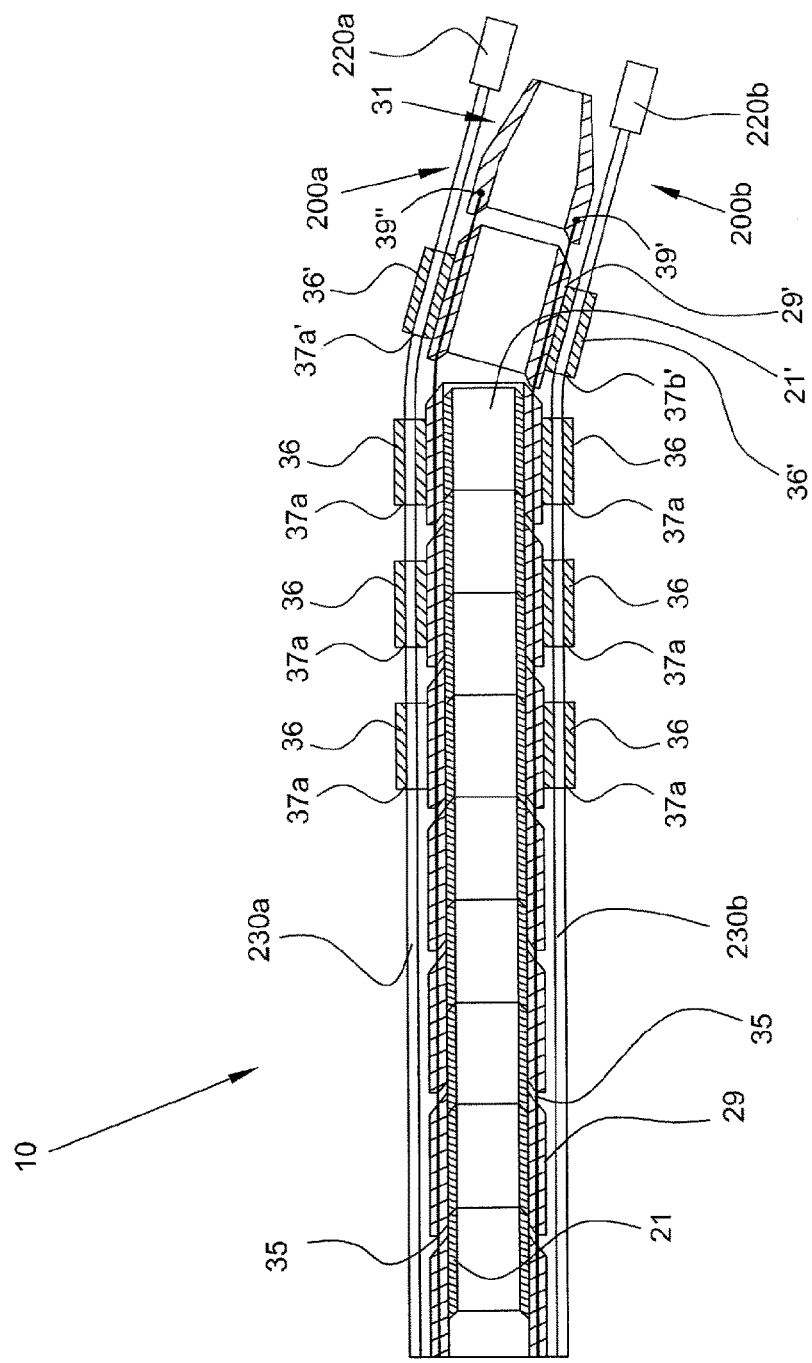
FIG. 12 illustrates a side sectional view of a tool support and two tools, in accordance with the present inventive concepts.

Referring now to FIG. 12, a sectional view of the tool support of FIGS. 10 and 11 is illustrated with the inner core retracted with its distal link just proximal to the last outer link prior to the distal link. Distal most inner link 21' has been retracted, such as via one or more cables, not shown but controlled by a controller of the present invention, such that no portion of inner link 21' is within outer link 29'. Cable 39' has been retracted such that distal link 31 and outer link 29' pivots toward the bottom of the page (cable 39" may be simultaneously advanced to support the rotation). Distal link 31 and outer link 29' may be fixedly attached, attachment not shown, such that they remain in the linear alignment shown in FIG. 12. Distal flange 36' has rotated with outer link 29', and working ends 220*a* and 220*b* of tools 200*a* and 200*b* rotate accordingly. Camera 50, not shown but described in reference to FIG. 10*a*, has its viewing window moved proportional with the movement of distal link 31, outer link 29' and flange 36'.

Figures 13, 13A:
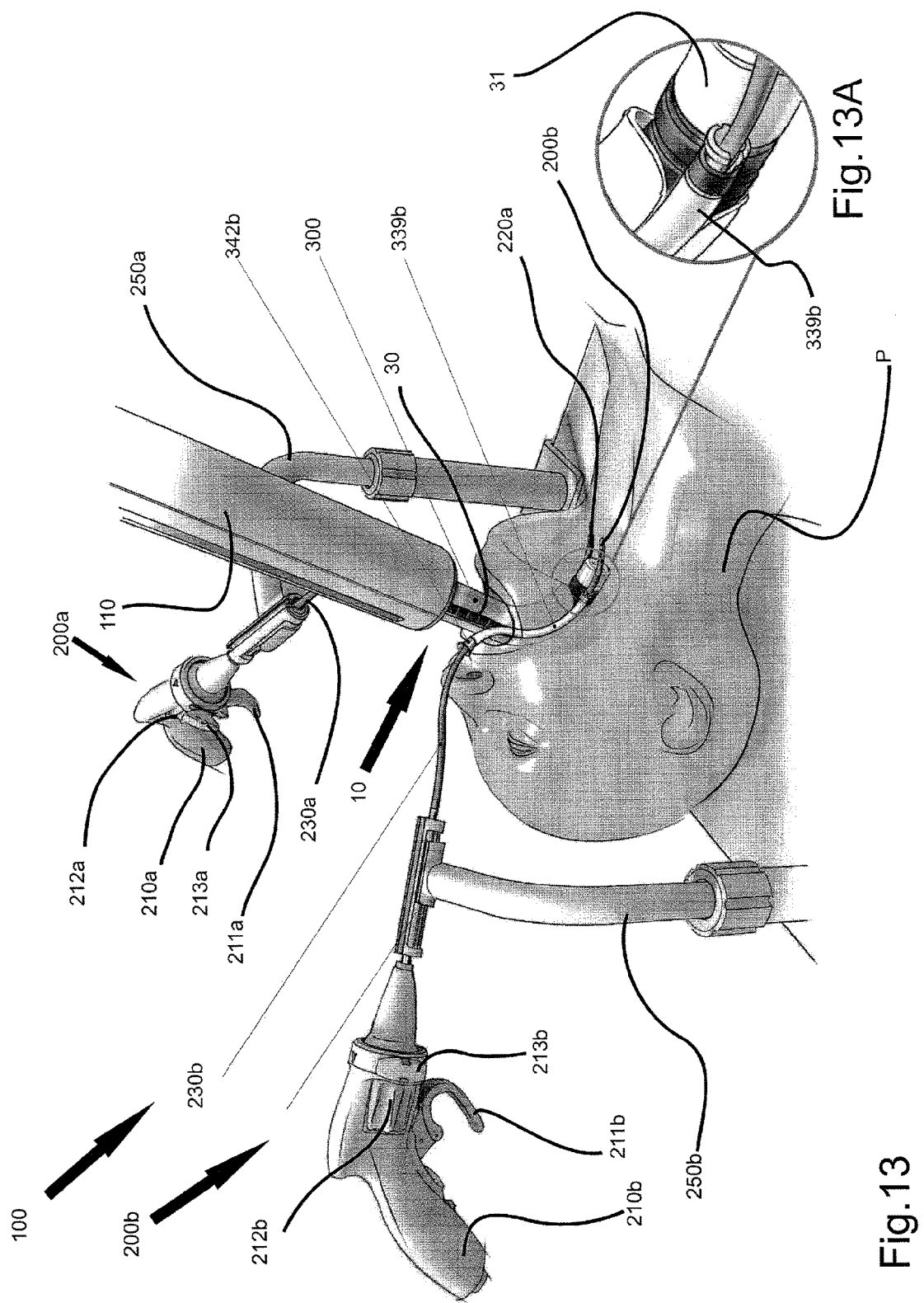
FIG. 13 illustrates a perspective view of a system for performing a medical procedure, in accordance with the present inventive concepts.
FIG. 13A illustrates a close-up perspective view of a system for performing a medical procedure, in accordance with the present inventive concepts.

Referring now to FIGS. 13 and 13A, a perspective view of a system in accordance with the present inventive concepts is illustrated inserted into the esophagus of a patient. System 100 includes probe 10 which has integral and/or feeder 110 attached to tool support introducer 300. Outer sleeve 30 is slidingly received by tool support 300, with both positioned in the esophagus of patient P. Guide tubes 339*a* and 339*b* (339*a* not shown), each of which include a lumen or other guide hole of the present invention therethrough, are attached to outer sleeve 30 at or near distal link 31. Tool 200*b*, which includes controls 211*b*, 212*b* and 213*b* as have been described hereabove, is supported by tool holder 250*b* such that shaft 230*b* can be can be advanced, retracted, and/or rotated. Tool 200*b* shaft 230*b* is inserted through funnel 342*b* and into a guide tube 339*b*. Tool 200*a* is similarly positioned and inserted.

Figure 14A:
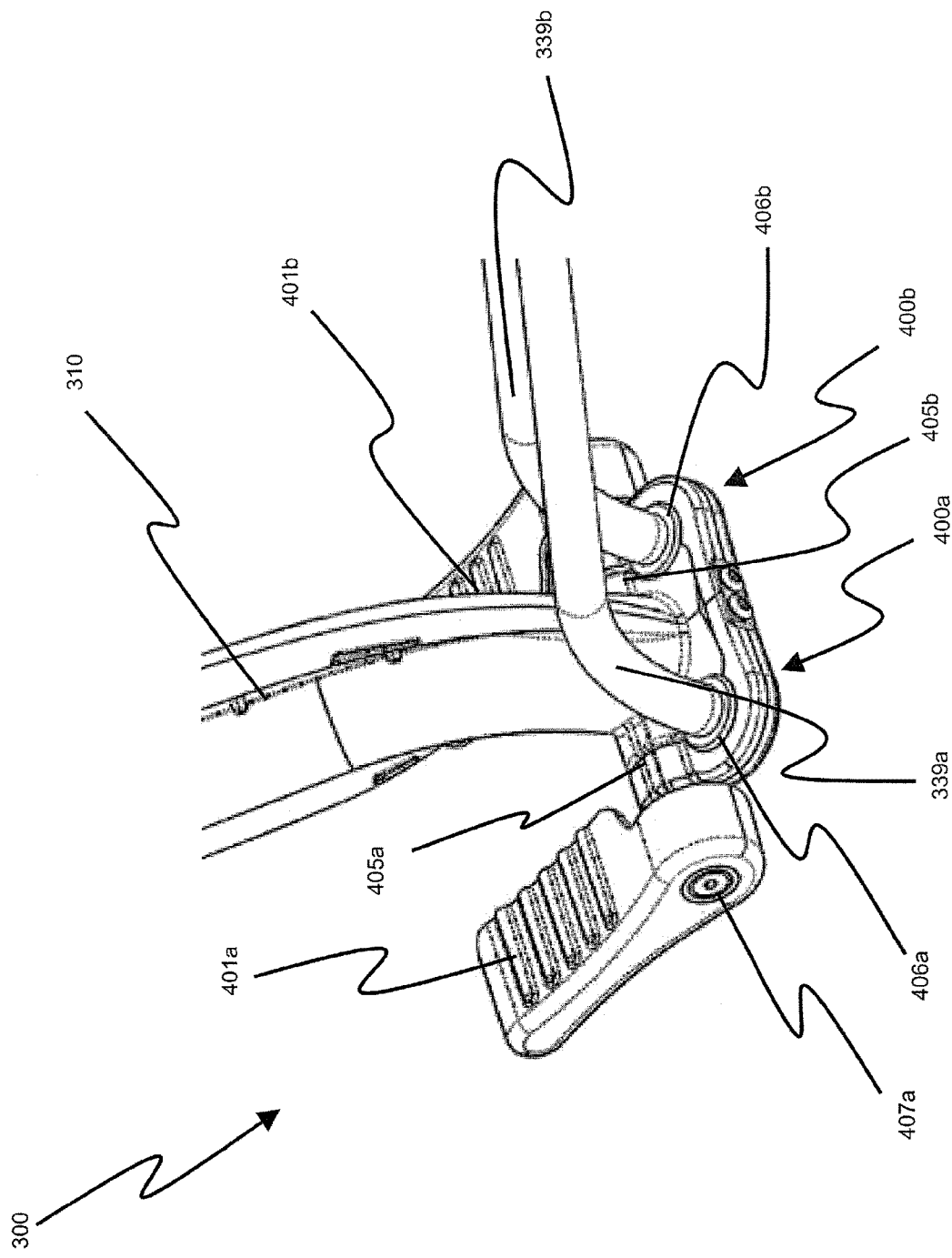
FIG. 14A illustrates a perspective view of a tool support introducer including lockable, rotatable couplers, in accordance with the present inventive concepts.
Figure 14B:
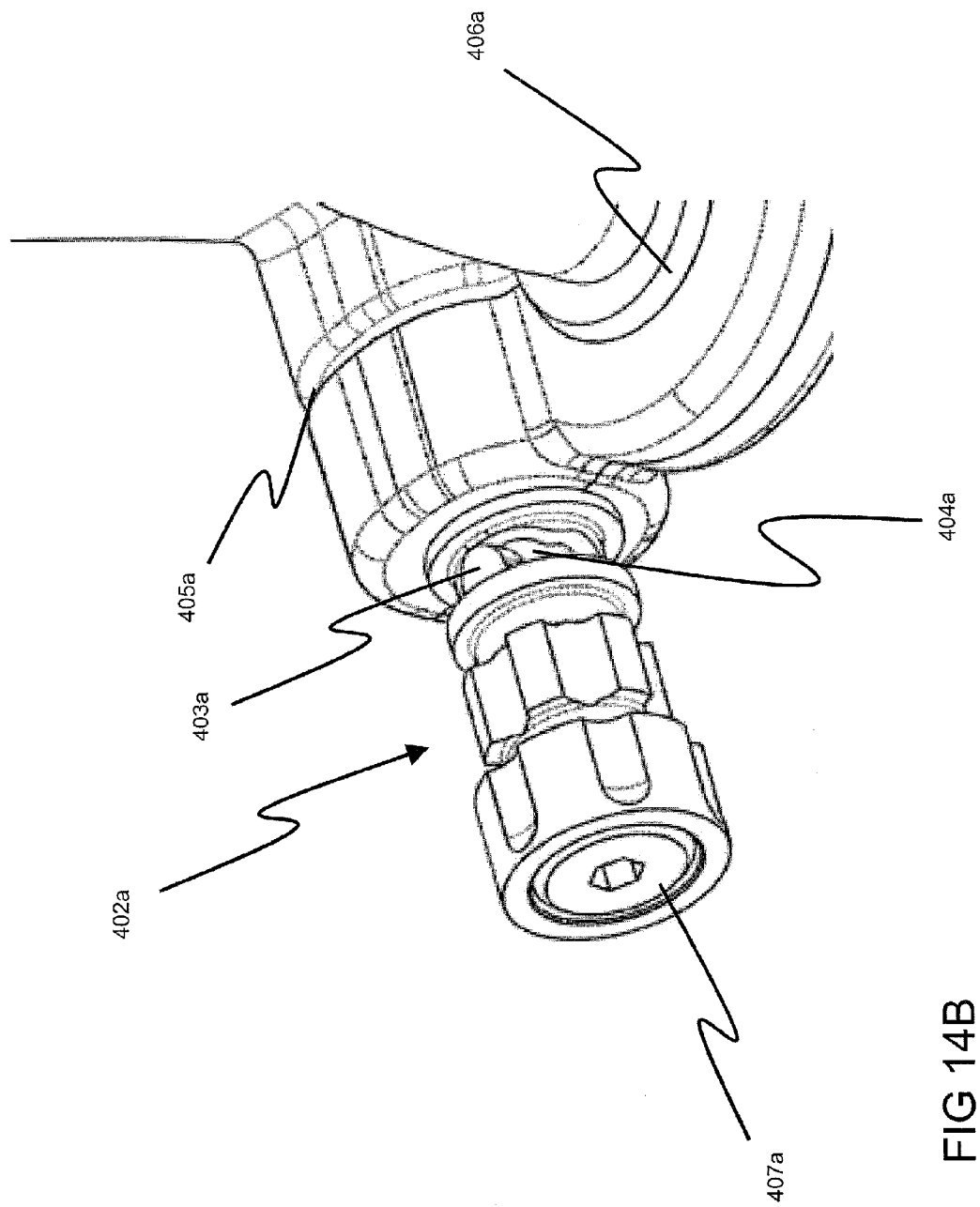
FIG. 14B illustrates a detailed view of the lockable, rotatable couplers of FIG. 14A, in accordance with the present inventive concepts.

Referring now to FIG. 14A, a tool support introducer including lockable, rotatable couplers is illustrated. FIG. 14B illustrates a detailed view of the components of the lockable, rotatable couplers, with some components removed for clarity. Introducer 300 includes shaft 310, typically including a lumen, not shown, but sized to fit a probe, for example, probe 10 as described in reference to FIG. 1 hereabove.

Introducer 300 includes two guide tubes 339*a* and 339*b*, each configured for insertion of the shaft of a tool, not shown but typically a tool configured to controllably manipulate and/or operate one or more of: a grasper; a cutter; an ablater; a cauterizer; a drug delivery element; a radiation source; a sensor such as an EKG electrode, a pressure sensor or blood sensor; a magnet; a heating element; a cryogenic element; and combinations of these. Alternatively or additionally, guide tubes 339 and 339 may be configured for insertion of an additional guide tube, such as a semi-rigid guide tube or a flexible guide tube that can extend and provide support beyond the distal ends of guide tube 339*a* or 339*b*. Guide tubes 339*a* and 339*b* are connected to lockable, rotatable couplers 400*a* and 400*b*, respectively. Couplers 400*a* and 400*b*, typically cam-lockable ball joints, may be detachable. Coupler 400*a* includes an actuator, lever 401*a*. Movement of lever 401*a* in one direction, for example, a downward direction relative to a user, rotates cam sleeve 402*a* to apply a force that linearly displaces cam 403*a* which closes gap 405*a*, locking ball 406*a* in place, thus placing guide tube 339*a* in a locked state. In this locked state, movement of guide tube 339*a* is prevented, including when a force is applied, such as a when a force is applied during manipulation of a tool whose shaft has been inserted through guide tube 339*a*.

Conversely, movement of lever 401*a* in the opposite direction, i.e. an upward direction relative to the user, rotates cam sleeve 402*a* to release the force applied to cam 403*a* allowing cam 403*a* to linearly displace in the opposite direction, increasing gap 405*a*. The increase in gap 405*a* releases the force applied to ball 406*a*, placing guide tube 339*a* in an unlocked state. In this unlocked state, guide tube 339*a* remains frictionally engaged with coupler 400*a*, such that guide tube 339*a* is gravitationally supported but free to move (e.g. by the hand of an operator) relative to ball 406*a*. Additionally, coupler 400*a* may include a screw, including screw head 407*a*, that is fixed in place, such as via an adhesive, to prevent loosening. Screw head 407*a* can provide a bearing surface for cam sleeve 402*a*. Coupler 400*a* includes insert 404*a* that provides a surface against which cam 403*a* translates.

Coupler 400*b* components are similar to that of coupler 400*a*, for example, coupler 400*b* includes lever 401*b*, gap 405*b*, and ball 406*b*. Additionally, the functionality of the coupler 400*b* and its components are typically the same or similar to that of coupler 400*a*.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the inventive concepts, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A system for performing a medical procedure comprising: at least one tool comprising a proximal portion and a distal portion with a distal end; a tool support comprising at least one radially extending side lobe constructed and arranged to support the distal portion of the at least one tool, wherein the tool support comprises a highly articulated probe, the probe comprising: an outer sleeve comprising a first plurality of links, the outer sleeve including a proximal link, a distal link, and a plurality of intermediate links between the proximal link and the distal link; and an inner core comprising a second plurality of links, wherein the at least one side lobe extends radially from and is integral with an outermost surface of at least one of the intermediate links of the outer sleeve, wherein the distal link is manipulated by a device controller and articulates independently of the intermediate link of which the at least one side lobe radially extends and further articulates relative to the distal end of the at least one tool extending through the at least one side lobe; the device controller constructed and arranged to create control signals based on operator input and to manipulate a distal end of the probe including the first plurality of links of the outer sleeve of the probe from which the at least one side lobe radially extends; and a controller constructed and arranged to receive the control signals and manipulate the tool support including one of the first plurality of links of the outer sleeve of the probe from which the at least one side lobe radially extends based on the received control signals.

2. The system of claim 1 wherein the highly articulated probe further comprises,
a first cable extending through either said second plurality of links of the inner core or said first plurality of links of the outer sleeve and a plurality of cables running through the other of said plurality of links of the inner core or said plurality of links of the outer sleeve.

3. The system of claim 1 further comprising a feeder assembly constructed and arranged to alternate each of said inner core and outer sleeve between a limp mode and a rigid mode, for advancing and retracting said inner core and outer sleeve, and for steering at least one of said inner core and outer sleeve.

4. The system of claim 1 wherein the tool support comprises a highly articulated probe, wherein the highly articulated probe comprises at least a portion that is controllably rigid and flexible.

5. The system of claim 1 wherein the at least one radially extending side lobe comprises multiple radially extending side lobes each constructed and arranged to support the distal portion of the at least one tool.

6. The system of claim 1 further comprising at least one guide tube constructed and arranged to slidingly receive the at least one tool.

7. The system of claim 6 wherein the tool support comprises a distal portion and the at least one guide tube is attached to said distal portion.

8. The system of claim 7 wherein the at least one guide tube is removably attached to said distal portion.

9. The system of claim 6 further comprising a tool support introducer wherein the at least one guide tube is attached to at a region of the tool support introducer that is proximal to the at least one radially extending side lobe.

10. The system of claim 9 wherein the at least one guide tube is removably attached to the tool support introducer.

11. The system of claim 6 wherein the at least one guide tube comprises at least one of: a flexible portion; a rigid portion; a rigid portion and a flexible portion; or a rotatable coupler.

12. The system of claim 6 wherein the at least one guide tube comprises a funnel shaped opening.

13. The system of claim 6 wherein the at least one guide tube comprises a first guide tube, wherein the at least one tool comprises a first tool, and wherein the system further comprises a second tool and a second guide tube constructed and arranged to slidingly receive the second tool.

14. The system of claim 1 wherein the controller comprises a cable tensioning assembly.

15. The system of claim 1 wherein the at least one tool distal portion comprises a functional element selected from the group consisting of: grasper; cutter; ablater; cauterizer; drug delivery element; radiation source; sensor such as a EKG electrode, pressure sensor or blood sensor; magnet; heating element; cryogenic element; and combinations thereof.

16. The system of claim 1 further comprising a tool holder constructed and arranged to attach to the at least one tool proximal portion.

17. The system of claim 1 further comprising a tool support introducer, wherein the tool support introducer comprises a tube constructed and arranged to slidingly receive the tool support.

18. The system of claim 17 wherein the tool support introducer is constructed and arranged for insertion into the esophagus.

19. The system of claim 1, wherein in response to a first control signal of the device controller, the distal link articulates independently of the intermediate link of which the at least one side lobe radially extends so that the at least one side lobe is stationary relative to the articulation of the distal link, and wherein in response to a second control signal of the device controller, the distal link and the intermediate link articulate together so that that at least one side lobe articulates with distal link and the intermediate link.

* * * * *

UNITED STATES PATENT AND TRADEMARK OFFICE
CERTIFICATE OF CORRECTION

PATENT NO. : 9,901,410 B2  
APPLICATION NO. : 13/812324  
DATED : February 27, 2018  
INVENTOR(S) : Arnold Oyola et al.

It is certified that error appears in the above-identified patent and that said Letters Patent is hereby corrected as shown below:

In the Claims

Claim 9, Column 15, Line 2, please delete "to" after "tube is attached"

Claim 15, Column 15, Line 23, please delete "a" after "sensor such as" and insert --an--

Claim 19, Column 16, Line 21, please delete the second instance of "that" before "at least one side lobe"

Claim 19, Column 16, Line 22, please insert --the-- before "distal link and the intermediate link"

Signed and Sealed this  
Twenty-sixth Day of June, 2018

Andrei Iancu  
*Director of the United States Patent and Trademark Office*